(12) United States Patent
Zemlicka et al.

(10) Patent No.: US 7,393,855 B2
(45) Date of Patent: Jul. 1, 2008

(54) 2,2-BIS-(HYDROXYMETHYL)CYCLOPROPYLIDENEMETHYL-PURINES AND PYRIMIDINES AS ANTIVIRAL AGENTS

(75) Inventors: Jiri Zemlicka, Warren, MI (US); Shaoman Zhou, Detroit, MI (US); John C. Drach, Ann Arbor, MI (US)

(73) Assignees: The Regents of the University of Michigan, Ann Arbor, MI (US); Wayne State University, Detroit, MI (US)

( * ) Notice: Subject to any disclaimer, the term of this patent is extended or adjusted under 35 U.S.C. 154(b) by 0 days.

(21) Appl. No.: 10/942,313

(22) Filed: Sep. 15, 2004

(65) Prior Publication Data
US 2005/0113393 A1 May 26, 2005

Related U.S. Application Data

(63) Continuation of application No. PCT/US03/07916, filed on Mar. 14, 2003.

(60) Provisional application No. 60/364,518, filed on Mar. 15, 2002.

(51) Int. Cl.
*C07D 473/32* (2006.01)
*C07D 473/16* (2006.01)
*A61K 31/522* (2006.01)

(52) U.S. Cl. .............................. 514/263.1; 514/263.37; 514/263.4; 544/265; 544/276; 544/278

(58) Field of Classification Search .................. 544/265, 544/276, 278; 514/263.4, 263.37, 263.3, 514/263.1
See application file for complete search history.

(56) References Cited

U.S. PATENT DOCUMENTS 6,352,991 B1 3/2002 Zemlicka et al.
7,183,268 B2 2/2007 Zemlicka et al.

OTHER PUBLICATIONS

Cheng et al., Reactions of Methylenecyclopropanes with a Diethylzinc-Bromoform System, and the Utilization for Synthesis of a Novel Cyclopropylidene-Nucleoside, Tetrahedron Letters, vol. 38, No. 2, pp. 9005-9008, 1997.*
Douglar, Jr. Introduction to Viral Diseases, Cecil Textbook of Medicine, 20th Edition, vol. 2, pp. 1739-1747, 1996.*
Goff, PubMed Abstract (J Gene Med. 3(6):517-28) Nov.-Dec. 2001.*
Bosseray et al., PubMed Abstract (Pathol. Biol. 50(8):483-92), Oct. 2002.*
Razonable et al., PubMed Abstract (Herpes 10(3):60-5), Dec. 2003.*
Kumar et al., 5-(1-substituted) alkyl pyrimidine nucleosides as antiviral (herpes) agents, Current Medicinal Chemistry, vol. 11, No. 20, pp. 2749-2766, 2004.*
Baker, et al.; "Utilization of the D- and L-Isomers of Methionine and Methionine Hydroxy Analogue as Determined by Chick Bioassay" *Journal of Nutrition* 1980, 110(5), 959-964.

Silverman; "Prodrugs and Drug Delivery Systems", Chapter 8 in "The Organic Chemistry of Drug Design and Drug Action," pp. 352-401.
Chen, et al., "Structure-Activity Relationships of (S,Z)-2-Aminopurine Methylenecyclopropane Analogues of Nucleosides, Variation of Purine-6 Substituents and Activity against Herpesviruses and Hepatitis B Virus" *J. Med. Chem.* 2003, 46, 1531-1537.
Chen, et al.; "Synthesis of (Z)-(2,3-bis-Hydroxymethyl)-methylenecyclopropane Analogues of Purine Nucleosides" *Nucleosides, Nucleotides & Nucleic Acids*, 2003, 22(3), 265-274.
Franchetti, et al.; "Synthesis and Evaluation of the Anti-HIV Activity of Aza and Deaza Analogues of IsoddA and Their Phosphates as Prodrugs" J. Med. Chem. 1994, 37, 3534-3541.
Innaimo, et al.; "Identification of BMS-200475 as a Potent and Selective Inhibitor of Hepatitis B Virus," *Antimicrobial Agents and Chemotherapy* 1997, 41(7), 1444-1448.
Kern, et al.; "In Vitro Activity and Mechanism of Action of Methylenecyclopropane Analogs of Nucleosides against Herpesvirus Replication" *Antimicrobial Agents and Chemotherapy* 2005, 49(3), 1039-1045.
Kern, et al.; "Oral Activity of a Methylenecyclopropane Analog, Cyclopropavir, in Animal Models for Cytomegalovirus Infections" *Antimicrobial Agents and Chemotherapy* 2004, 48(12), 4745-4753.
McGuigan, et al.; "Intracellular Delivery of Bioactive AZT Nucleotides by Aryl Phosphate Derivatives of AZT" *J. Med. Chem.* 1993, 36, 1048-1052.
Mitsuya, et al.; "3'-Azido-3'-deoxythymidine (BW A509U): An antiviral agent that inhibits the infectivity and cytopathic effect of human T-lymphotropic virus type III/lymphadenopathy- associated virus in vitro" *Proc. Natl. Acad. Sci. USA* 1985, 82, 7096-7100.

(Continued)

*Primary Examiner*—Deepak Rao
(74) *Attorney, Agent, or Firm*—DaAnn F. Smith, Esq.; Foley Hoag LLP

(57) ABSTRACT

Compounds which are active against viruses have the following formulas:

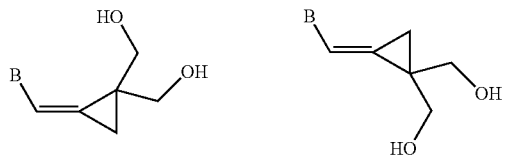

wherein B is a purine or pyrimidine heterocyclic ring or base. In a preferred embodiment, the purine include 6-aminopurine (adenine), 6-hydroxypurine (hypoxanthine), 2-amino-6-hydroxypurine (guanine), 2,6-diamino-purine, 2-amino-6-azidopurine, 2-amino-6-halo substituted purines such as 2-amino-6-chloropurine, 2-amino-6-fluoropurine, 2-amino-6-alkoxypurines such as 2-amino-6-methoxypurine, 2-amino-6-cyclopropylaminopurine, 2-amino-6-alkylamino or 2-amino-6-dialkylamino substituted purines, 2-amino-6-thiopurine, 2-amino-6-alkylthio substituted purines, 3-deazapurines, 7-deazapurines and 8-azapurines. The pyrimidine incorporates cytosine, uracil and thymine, 5-halo substituted cytosines and uracils, 5-alkyl substituted cytosines and uracils including derivatives with a saturated or unsaturated alkyl group and 6-azapyrimidines.

9 Claims, 4 Drawing Sheets

OTHER PUBLICATIONS

Oatis, et al.; "Ring-Hydroxylated Propranolol: Synthesis and β-Receptor Antagonist and Vasodilating Activities of the Seven Isomers" *J. Med. Chem.* 1981, 24, 309-314.

Powell, et al.; "Metabolism of 5(S)-Hydroxy-6,8,11,14-eicosatetraenoic Acid and Other 5(S)- Hydroxyeicosanoids by a Specific Dehydrogenase in Human Polymorphonuclear Leukocytes" *The Journal of Biological Chemistry* 1992, 267(27), 19233-19241.

Schaeffer, et al.; "Enzyme Inhibitors. 26. Bridging Hydrophobic and Hydrophilic Regions on Adenosine Deaminase with Some 9-(2-Hydroxy-3-alkyl)adenines" *Journal of Medicinal Chemistry* 1974, 17(1), 6-8.

Schaeffer, et al.; "9-(2-Hydroxyethoxymethyl) guanine activity against viruses of the herpes group" *Nature* 1978, 272, 583-585.

Zemlicka, et al., "Methylenecyclopropane analogs of nucleotides as antiviral agents" (Schinazi and Liotta, eds), *Frontiers in Nucleoside and Nucleic Acids*, IHL Press 2004, 267-307.

Zhou, et al.; "Synthesis and Antiviral Activity of (Z)- and (E)-2,2-[Bis(hydroxymethyl) cyclopropylidene] methylpurines and-pyrimidines: Second-Generation Methylenecyclopropane Analogues of Nucleosides" *J. Med. Chem.* 2004, 47, 566-575.

\* cited by examiner

Figure 1

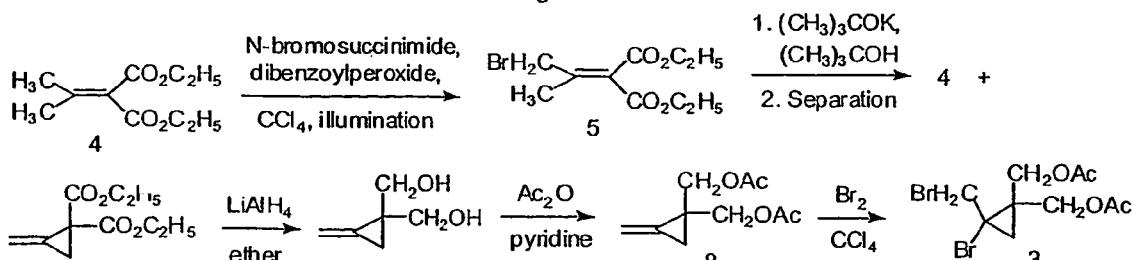

Ac = acetyl

Figure 2

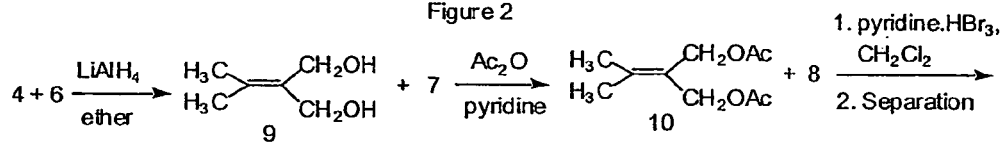

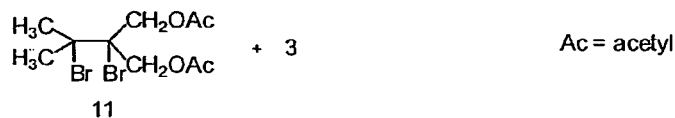

Ac = acetyl

Figure 3

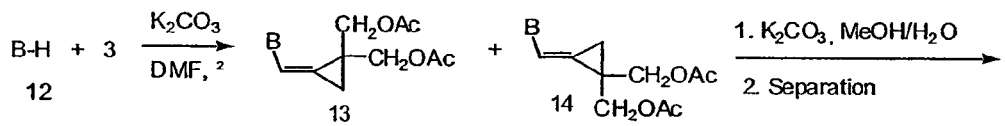

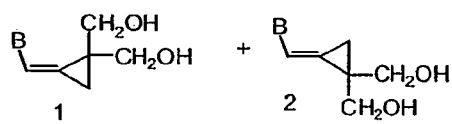

DMF = N,N-Dimethylformamide
Ac = Acetyl

Series a: B = adenin-9-yl
Series b: B = 2-amino-6-chloropurin-9-yl
Series c: B = guanin-9-yl
Series d: B = $N^4$-acetylcytosin-1-yl
Series e: B = cytosin-1-yl
Series f: B = thymin-1-yl
Series g: B = 2-amino-6-methoxypurin-9-yl
Series h: B = 2-amino-6-cyclopropylaminopurin-9-yl
Series i: B = 2-amino-6-allylaminopurin-9-yl
Series j: B = 2-amino-6-propargylaminopurin-9-yl
Series k: B = 2-amino-6-cyclopropylmethylamino-purin-9-yl
Series l: B = 2-amino-6-propyloxypurin-9-yl
Series m: B = 2-amino-6-allyloxypurin-9-yl
Series n: B = 2-amino-6-propylthiopurin-9-yl
Series o: B = 2,6-diaminopurin-9-yl
Series p: B = 2-amino-6-fluoropurin-9-yl Ac = Acetyl
TMS = (CH₃)₃Si Figure 8
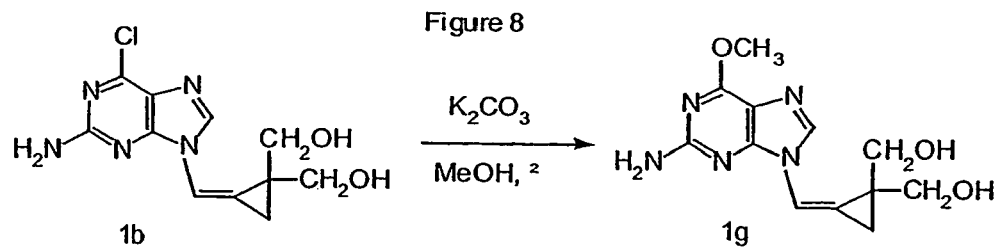
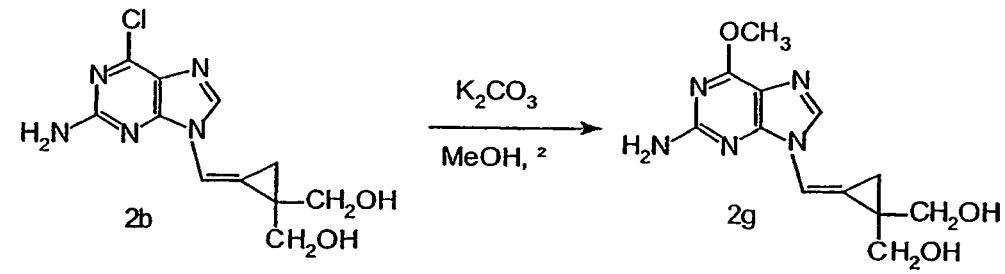
Figure 9
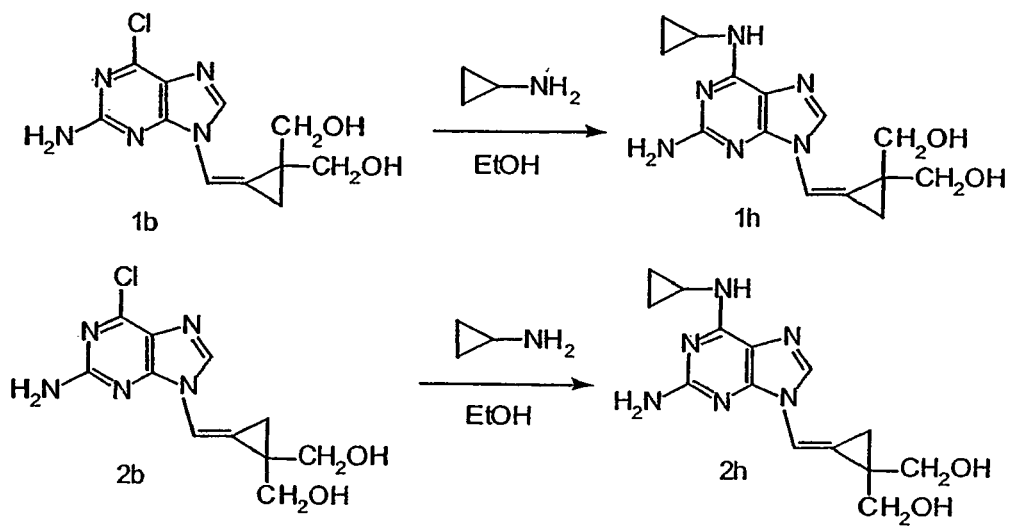
Figure 10
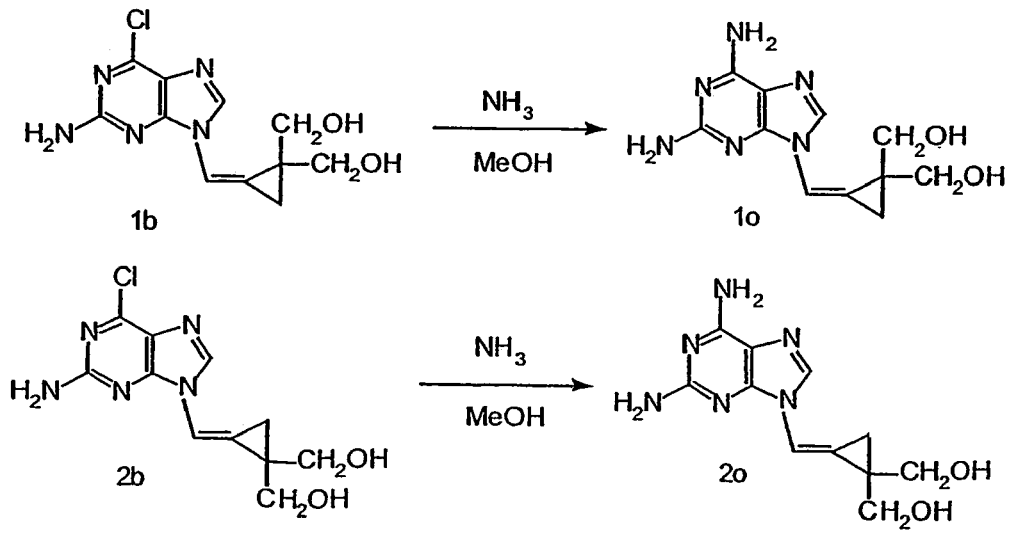

2,2-BIS-(HYDROXYMETHYL)CYCLOPRO-PYLIDENEMETHYL-PURINES AND PYRIMIDINES AS ANTIVIRAL AGENTS

RELATED APPLICATIONS

This patent application is a continuation of co-pending International Application No. PCT/US03/007916, filed Mar. 14, 2003, which claims the benefit of Provisional Application No. 60/364,518, filed Mar. 15, 2002, which is incorporated herein by reference.

SPONSORSHIP

Work on this invention was supported in part by the National Cancer Institute, Grant No. RO1 CA32779 and National Institute of Allergy and Infectious Diseases, Grant No. PO1-AI46390. The Government has certain rights in the invention.

FIELD OF THE INVENTION

The present invention relates to novel purine and pyrimidine compounds which have antiviral activity and methods of making and using those compounds.

BACKGROUND OF THE INVENTION

Viruses are the etiologic cause of many life-threatening human diseases. Of special importance are herpes viruses such as herpes simplex 1 (HSV-1), herpes simplex 2 (HSV-2), cytomegalovirus (CMV), Epstein-Barr virus (EBV), varicella zoster virus (VZV) and human herpes viruses 6, 7 and 8 (HHV-6, -7 and -8) which are associated with many common viral illnesses. The HSV-1 and HSV-2 infections are characterized by cold sores of skin, mouth or genital region. After primary infection, the virus is harbored in neural cells and can reappear later in the life of a patient. Human CMV (HCMV) infection is a life-long affliction which can result in morbidity and mortality. These pathologies include microcephaly, hepatosplenomegaly, jaundice, encephalitis, infections of the newborn infants or fetuses in utero, and infections of immunocompromised hosts. HCMV infection is responsible for retinitis, gastritis and pneumonitis in AIDS patients and HCMV-induced pneumonias or hepatitis are frequent and serious complications of organ or bone marrow transplants. EBV causes infectious mononucleosis and it is considered as the etiologic agent of nasopharyngeal cancer, immunoblastic lymphoma, Burkitt's lymphoma and hairy leukoplakia. VZV causes chicken pox and shingles. Although in children the chicken pox is usually a non-fatal disease, the recurrent form of this infection, shingles, may in advanced stage lead to paralysis, convulsions and ultimately death. Again, in immunocompromised patients the infection with VZV is a serious complication. Human herpes virus 6 (HHV-6) which is commonly associated with children's rash was also identified in acquired immunodeficiency syndrome (AIDS) patients and it may be a cofactor in the pathogenesis of AIDS in hosts infected with human immunodeficiency virus (HIV). Levine, A. J. *Viruses*, Ch. 4, W. H. Freeman & Co., New York, pp. 67-85 (1992); *Human Herpesvirus Infections*, Raven Press, New York (1986); Schirmer, E. C., et al., *Proc. Natl. Acad. Sci. USA* 88:5922-5926 (1992). Human herpes virus 8 (HHV-8) was identified in patients with Kaposi sarcoma, a fatal affliction accompanying AIDS. Chang, Y., et al., *Science* 266: 1865-1869 (1994).

HIV is the underlying cause of AIDS, a world-wide epidemic with fatal consequences. According to the Joint United Nations Programme on HIV/AIDS, 40 million people are estimated to be living with HIV/AIDS at the end of 2001. During that same year, AIDS caused the deaths of an estimated 3 million people.

Hepatitis B virus (HBV) is a virus that causes chronic disease responsible for serious liver damage, including cirrhosis of the liver, cancer, organ failure and ultimately, death. It is estimated that approximately 300 million people worldwide are infected with HBV. According to the CDC, there are approximately 1.25 million Americans chronically infected with HBV. Although use of a prophylactic vaccine has reduced the incidence of new HBV infections, there continues to be a need for an effective therapeutic drug.

Various derivatives of nucleoside analogues have been found to exhibit antiviral activity. Notably, acyclovir (Zovirax) and and its prodrug valacyclovir (Valtrex) are approved drugs for infections caused by HSV-1 and HSV-2. *Acyclovir Therapy for Herpesvirus Infections* (Baker, Ed.), M. Dekker, New York (1990); Against HCMV, four drugs are currently available: Ganciclovir (Cytovene), cidofovir (Vistide), antisense oligonucleotide fomivirsen (Vitravene) and foscarnet (Foscavir). However, only ganciclovir is effective orally but it requires large doses and produces potentially serious adverse effects such as bone marrow suppression. *Ganciclovir Therapy for Cytomegalovirus Infection*(Spector, S. S., Ed.), M. Dekker, New York (1991). A considerable effort went into design, synthesis and biological investigation of analogues of these drugs as well as in development of new antiviral agents. Larsson, A., et al., *Antimicrob. Agents & Chemother*. 30:598-605 (1986); Ashton, W. T., et al., *J. Med. Chem*. 31:2304-2315 (1988). Cidofovir and fomivirsen are approved only for topical application against retinitis in AIDS patients and foscarnet is used only by intravenous route and it leads to characteristic toxicity.

Current drugs for AIDS include AZT (zidovudine, Retrovir), ddI (didanosine, Videx), ddC (zalcitabine, Hivid) and d4T (stavudine, Zerit). De Clercq, E., *J. Med. Chem*. 38:2491-2517 (1995). Allenic nucleoside analogues such as adenallene and cytallene are examples of anti-HIV agents containing an unsaturated alkyl group. U.S. Pat. No. 4,935,427; Zemlicka, J., *Allenols Derived from Nucleic Acid Bases—a New Class of Anti-HIV Agents: Chemistry and Biological Activity in Nucleosides and Nucleotides as Antitumor and Antiviral Agents* (Chu, C. K.; Baker, D. C., Eds.), Plenum Press, New York, pp. 73-100 (1993). For HBV, alpha interferon and 3TC (lamivudine; Epivir) are two drugs licensed for the treatment of persons with chronic HBV infection. Unfortunately, only about 40% of patients respond to these drugs and resistance is a growing problem.

Particular 2-hydroxymethylcyclopropylidenemethylpurines and their utility against certain viruses have been described elsewhere (see, for example, co-owned U.S. Pat. No. 6,352,991; Qiu, Y. L., et al., *J. Med. Chem*. 41:10-23 (1998); Antiviral Chem. Chemother. 9:341-352 (1998)). However, there continues to be a need for novel compounds which are active against pathogenic viruses, including HCMV, HSV-1, HSV-2, HHV-6, HIV, and hepatitis B virus (HBV).

SUMMARY OF THE INVENTION

The present invention describes novel 2,2-bis-(hydroxymethyl)cyclo-propylidenemethyl derivatives and heterocyclic compounds, prodrugs and pharmacologically acceptable salts thereof. These compounds which have been found to be useful antiviral agents and are effective against HCMV, HSV-1, HSV-2, HIV, EBV and HBV, as well as against other mammalian viruses. The compounds of the present invention have the following Formulas:

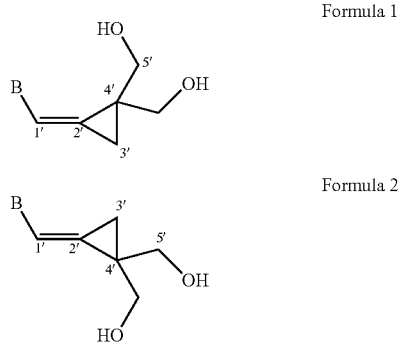

wherein B is a purine or pyrimidine heterocyclic ring or base. In a preferred embodiment, the purine includes 6-aminopurine (adenine), 6-hydroxypurine (hypoxanthine), 2-amino-6-hydroxypurine (guanine), 2,6-diamino-purine, 2-amino-6-azidopurine, 2-amino-6-halo substituted purines such as 2-amino-6-chloropurine, 2-amino-6-fluoropurine, 2-amino-6-alkoxypurines such as 2-amino-6-methoxypurine, 2,6-diaminopurine, 2-amino-6-cyclopropylaminopurine, 2-amino-6-alkylamino or 2-amino-6-dialkylamino substituted purines, 2-amino-6-thiopurine, 2-amino-6-alkylthio substituted purines, 3-deazapurines, 7-deazapurines and 8-azapurines. The pyrimidine incorporate cytosine, uracil and thymine, 5-halo substituted cytosines and uracils, 5-alkyl substituted cytosines and uracils including derivatives with a saturated or unsaturated alkyl group and 6-azapyrimidines.

Compositions useful for treatment of viral infections, such as HCMV, HSV-1, HSV-2, HHV-6, HIV, EBV and HBV contain an effective amount of at least one compound of Formulas 1 to 2 or a pharmaceutically acceptable salt thereof.

The present invention also includes a method for synthesizing compounds of Formulas 1 and 2 wherein B is a heterocyclic ring derived from purine or pyrimidine moiety such as 6-aminopurine (adenine), 6-hydroxypurine (hypoxanthine), 2-amino-6-hydroxypurine (guanine), 2,6-diaminopurine, 2-amino-6-azidopurine, 2-amino-6-halo substituted purines such as 2-amino-6-chloropurine, 2-amino-6-fluoropurine, 2-amino-6-alkoxypurines such as 2-amino-6-methoxypurine, 2,6-diaminopurine, 2-amino-6-cyclopropyl-aminopurine, 2-amino-6-alkylamino or 2-amino-6-dialkyl amino substituted purines, 2-amino-6-thiopurine, 2-amino-6-alkylthio substituted purines, 3- and 7-deazapurines such as 3- and 7-deazaadenine, 8-azapurines such as 8-azaadenine; cytosine, uracil, 5-halocytosine and 5-halouracil and related alkyl derivatives containing a saturated or unsaturated alkyl group at the 5-position), thymine, 6-azapyrimidines such as 6-azacytosine and wherein the alkyl side-chain attached to the heterocyclic ring is a 2,2-bis-(hydroxyl-methyl)cyclopropylidene methane moiety.

Additional objects, advantages, and features of the present invention will become apparent from the following description, taken in conjunction with the accompanying drawings.

BRIEF DESCRIPTION OF THE DRAWINGS

The various advantages of the present invention will become apparent to one skilled in the art by reading the following specification and by referencing the following drawings in which:

FIGS. 1 and 2 show two procedures for the synthesis of 1,1-dibromo-methyl-2,2-bis-(acetoxymethyl)cyclopropane (3);

FIG. 3 shows the synthesis of (Z)- and (E)-{[2,2-bis-(hydroxy-methyl)cyclopropylidene]methyl}purines and -pyrimidines of Formulas 1 and 2;

FIG. 8 shows the synthesis of (Z)-2-amino-6-methoxy-9-{[2,2-bis-(hydroxylmethyl)cyclopropylidene]methy}purine (1g) and (E)-2-amino-6-methoxy-9-{[2,2-bis-(hydroxylmethyl)cyclopropylidene]methyl-purine (2g);

FIG. 9 shows the synthesis of (Z)-2-amino-6-cyclopropylamino-9-{[2,2-bis-(hydroxyl-methyl)cyclopropylidene] methylpurine (1h) and (E)-2-amino-6-cyclopropylamino-9-{[2,2-bis-(hydroxymethyl)cyclo-propylidene]methylpurine (2h);

FIG. 10 shows the synthesis of (Z)-2,6-diamino-9-{[2,2-bis-(hydroxy-methyl)cyclopropylidene]methylpurine (1o) and (E)-2,6-diamino-9-{[2,2-bis-(hydroxymethyl)cyclopropylidene]methylpurine (2o)

DETAILED DESCRIPTION OF THE PREFERRED EMBODIMENTS

Figure 4:
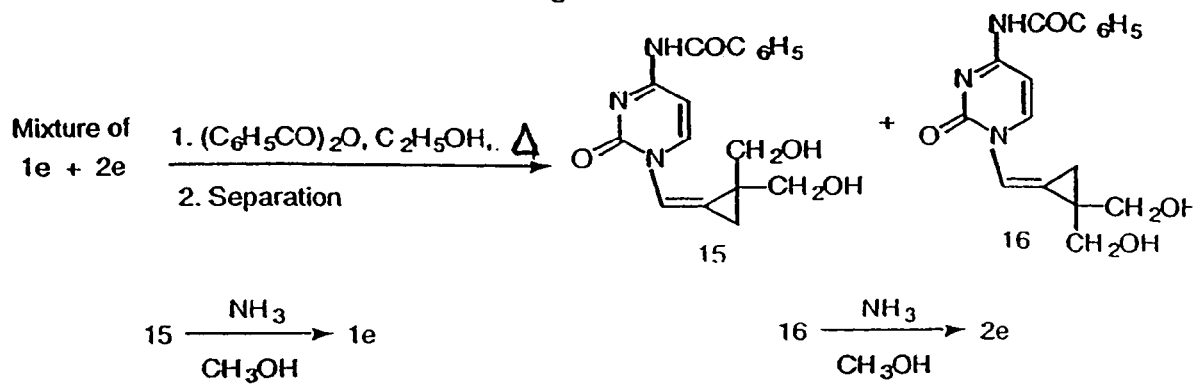
FIG. 4 shows the method for separation of (Z)-1-{[2,2-bis-(hydroxy-methyl)cyclopropylidene]methyl]}cytosine (1e) and (E)-{[2,2-bis-(hydroxy-methyl)cyclopropylidene]methyl}cytosine (2e)
Figure 5:
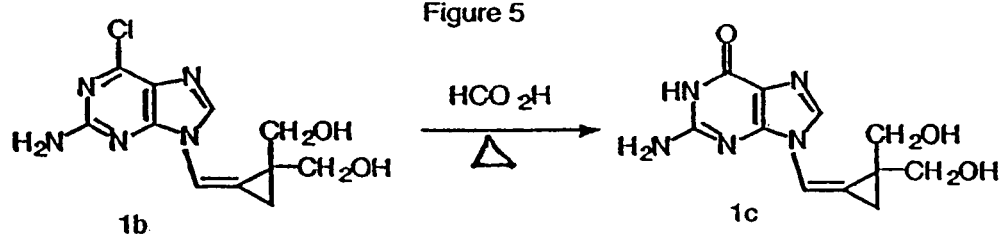
FIG. 5 shows the hydrolysis of (Z)-2-amino-6-chloro-9-{[2,2-bis-(hydroxylmethyl)cyclopropylidene]methyl}purine (1b) to (Z)-9-{[2,2-bis-(hydroxymethyl)cyclopropylidene]methyl}guanine (1c)

As used herein, the following terms shall be defined as follows (unless otherwise noted):

"Alkyl" shall mean a saturated straight chain or branched, primary, secondary, or tertiary hydrocarbon radical that is fully saturated, typically $C_1$-$C_{18}$, preferably $C_1$-$C_{10}$, and more preferably $C_1$-$C_6$ Preferred alkyl groups include, without limitation, methyl, ethyl, propyl, butyl, pentyl, hexyl, isopropyl, isobutyl, sec-butyl, t-butyl, isopentyl, amyl, and t-pentyl. For the purposes of this invention, any carbon in the alkyl moiety may be replaced with oxygen (O), sulfur (S), or nitrogen (N).

"Cycloalkyl" shall mean a mono-, bi- or polycyclic alkyl radical. For convenience, the term "cycloalkyl" shall also expressly include cycloalkenyl cycloalkynyl radicals. A "branched cycloalkyl" shall mean a cycloalkyl ring in which one or more ring members are substituted with alkyl. In general, these rings shall typically be $C_3$-$C_{18}$, preferably $C_3$-$C_{10}$, and more preferably $C_3$-$C_{18}$.

"Halo" shall mean fluoro, chloro, bromo, or iodo.

"Heterocyclyl" shall mean a mono-, bi- or polycyclic radical containing one or more rings which may be saturated, unsaturated, or aromatic, wherein at least one ring contains one or more heteroatoms selected from nitrogen (N), oxygen (O), and sulfur (S). Heterocyclyl radicals typically have 3-18 total ring members and preferably 3-10 total ring members. Preferably, heterocyclyl radicals are monocyclic (preferably having 3-8 and more preferably, 3-6 ring members) or bicyclic (preferably having 6-12 ring members and more preferably, 8-10 ring members). Suitable heterocyclyl for use in the compounds of this invention include radicals of (without limitation) furan, dioxolane, thiophene, pyrrole, pyrazole, triazole, imidazole, pyrrolidine, pyran, pyridine, pyrimidine, morpholine, piperidine, oxazole, isoxazole, oxazoline, oxazolidine, oxathiazole, thiazole, isothiazole, thiadiazole, tetrazole, benzofuran, indole, isoindole, quinazoline, quinoline, isoquinoline, purine, pyrrolopyrimidine, pyrrazolopyrimidine, pteridine, ketal. In addition, heterocyclyl radicals may contain one or more substituents (i.e., a ring substituent, such as a halogen atom, an alkyl radical, or aryl radical) attached to a ring member atom of the heterocyclyl radical. All stable isomers of heterocyclyl groups are contemplated in this definition.

"Lower" shall mean the group to which it is applied preferably has 1-6, and more preferably 1-4, carbon atoms, except in the case of rings (such as cycloalkyl and heterocyclyl), in which case "lower" signifies 3-6 ring members.

"Patient" shall mean any warm-blooded mammal, including without limitation, a human.

"Pharmaceutically acceptable salts" shall mean those salts of any compound of this invention derived from an inorganic or organic acid or base recognized in the art as compatible for pharmaceutical compositions. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids such as oxalic, while not in themselves pharmaceutically acceptable, may be useful as intermediates in obtaining the compounds of the invention and their pharmaceutically acceptable acid addition salts. Salts derived from appropriate bases include alkali metal (e.g., sodium, potassium), alkaline earth metal (e.g., magnesium), ammonium and $NR_4^+$ (where R is a $C_{1-4}$ alkyl) salts, and the like. Reference to a compound according to the invention is understood to include any and all corresponding pharmaceutically acceptable salts thereof. For convenience, the terms "pharmaceutical" and "pharmaceutically acceptable" are understood to encompass compounds acceptable for the practice of veterinary medicine as well.

"Pharmaceutically acceptable carriers" for use in the formulations of this invention are carriers that are compatible with the other ingredients of the formulation and not deleterious to the recipient thereof.

"Therapy" and "therapeutic" shall mean treatment of an individual for a viral infection or disease. For convenience, these terms are also understood to encompass prophylactic or precautionary use or administration of a compound of this invention. Such precautionary or prophylactic use is exemplified by administration of an antiviral agent to an individual(s) suspected, but not proven, of having a viral infection or to an individual(s) susceptible to contracting a pathogenic viral infection due to contact with contaminated items, or contact with other individuals carrying a contagious viral disease.

All published documents referred to herein are expressly incorporated herein by reference.

The compounds of the present invention which have been found to be effective against herpes viruses such as human cytomegalovirus (HCMV) and herpes simplex virus type 1 (HSV-1), human immunodeficiency virus and hepatitis B virus, are compounds of Formulas 1 to 2, wherein B represents a heterocyclic ring derived from a purine moiety (preferably attached via the 9-position) or pyrimidine moiety (preferably attached via the 1-position) such as 6-aminopurine (adenine), 6-hydroxypurine (hypoxanthine), 2-amino-6-hydroxypurine (guanine), 2,6-diamino-purine, 2-amino-6-azidopurine, 2-amino-6-halo substituted purines such as 2-amino-6-chloropurine, 2-amino-6-fluoropurine, 2-amino-6-alkoxypurines such as 2-amino-6-methoxypurine, 2,6-diaminopurine, 2-amino-6-cyclopropylaminopurine, 2-amino-6-alkylamino or 2-amino-6-dialkylamino substituted purines, 2-amino-6-thiopurine, 2-amino-6-alkylthio substituted purines, 3- and 7-deazapurines such as 3- and 7-deazaadenine, 8-azapurines such as 8-azaadenine; cytosine, 5-halocytosine and 5-halouracil (wherein halo is bromo, chloro, iodo or fluoro) and related alkyl derivatives containing a saturated or unsaturated alkyl group at the 5-position), thymine, 6-azapyrimidines such as 6-azacytosine, wherein the alkyl side-chain attached to the heterocyclic ring is a 2,2-bis-(hydroxymethyl) cyclopropylidene-methane moiety.

The preferred compounds of the present invention are (Z)-9-{[2,2-bis-(hydroxyl-methyl)cyclopropylidene]methyl}adenine (1a), (Z)-9-{[2,2-bis-(hydroxymethyl)cyclo-propylidene]methyl}guanine (1c), (Z)-1-{[2,2-bis-(hydroxymethyl)cyclopropylidene]-methyl}cytosine (1e), (Z)-1-{[2,2-bis-(hydroxymethyl)cyclopropylidene]methyl}thymine (1f), (E)-9-{[2,2-bis-(hydroxymethyl)cyclopropylidene]methyl}adenine (2a), (E)-9-{[2,2-bis-(hydroxylmethyl)cyclopropylidene]methyl}guanine (2c), (Z)-2-amino-6-methoxy-9-{[2,2-bis-(hydroxymethyl)cyclopropylidene]-methyl}purine (1g) and (E)-2-amino-6-methoxy-9-{[2,2-bis-(hydroxy-methyl)cyclopropylidene]-methyl}purine (2g). The preferred compounds of the present invention are also (Z)-2-amino-6-cyclopropylamino-9-{[2,2-bis-(hydroxy-methyl)cyclopropylidene]methyl}purine (1h), (E)-2-amino-6-cyclopropylamino-9-{[2,2-bis-(hydroxymethyl)cyclopropylidene]methyl}purine (2h), (Z)-2-amino-6-allylamino-9-{[2,2-bis-(hydroxymethyl)cyclopropylidene]methyl}purine (1i), (E)-2-amino-6-allylamino-9-{[2,2-bis-(hydroxymethyl)cyclopropylidene]methyl}-purine (2i), (Z)-2-amino-6-propargylamino-9-{[2,2-bis-(hydroxymethyl)cyclo-propylidene]methyl}purine (1j), (E)-2-amino-6-propargylamino-9-{[2,2-bis-(hydroxymethyl)cyclopropylidene]methyl}purine (2j), (Z)-2-amino-6-cyclopropylmethylamino-9-{[2,2-bis-(hydroxymethyl)cyclopropylidene]-methyl}purine (1k), (E)-2-amino-6-cyclopropylmethylamino-9-{[2,2-bis-(hydroxymethyl)cyclopropylidene]methyl}purine (2k), (Z)-2-amino-6-propyloxy-9-{[2,2-bis-(hydroxymethyl)cyclopropylidene]methyl}purine (1l), (E)-2-amino-6-propyloxy-9-{[2,2-bis-(hydroxymethyl)cyclopropylidene]-methyl}purine (2l), (Z)-2-amino-6-allyloxy-9-{[2,2-bis-(hydroxymethyl)cyclopropylidene]methyl}purine (1m), (E)-2-amino-6-allyloxy-9-{[2,2-bis-(hydroxy-methyl)-cyclopropylidene]methyl}purine (2m), (Z)-2-amino-6-propylthio-9-{[2,2-bis-(hydroxymethyl)cyclopropylidene]methyl}purine (1n) and (E)-2-amino-6-propylthio-9-{[2,2-bis-(hydroxymethyl)cyclopropylidene]-methyl}purine (2n); (Z)-2,6-diamino-9-{[2,2-bis-(hydroxymethyl)cyclo-propylidene]methylpurine (1o), (E)-2,6-diamino-9-{[2,2-bis-(hydroxymethyl)-cyclopropylidene]methylpurine (2o), (Z)-2-amino-6-fluoro-9-{[2, 2-bis-(hydroxy-methyl)cyclopropylidene]methylpurine (1p); and (E)-2-amino-6-fluoro-9-{[2,2-bis-(hydroxymethyl)cyclopropylidene]methylpurine (2p).

The nomenclature of the compounds of the present invention follows standard conventions. The numbering of the cyclopropylidenemethane moiety attached to the heterocyclic ring B is shown in Formulas 1 and 2. The purine and pyrimidine rings are numbered as shown below:

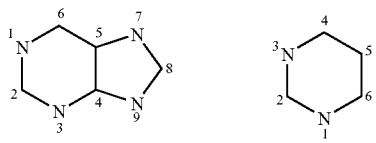

It is appreciated that heterocyclic rings containing hydroxy and amino groups are tautomeric with the corresponding oxo and imino compounds. For the sake of clarity, it is noted that Formula 1 is the Z-isomer and Formula 2 is the E-isomer of the novel 2,2-bis-(hydroxyl-methyl)cyclopropylidenemethyl compounds of this invention.

The syntheses of exemplified compounds of the present invention are summarized in FIGS. 1 to 8. Generally, suitably O-protected 1-halo-1-halomethyl-2,2-bis-(hydroxymethyl) cyclopropanes can serve as alkylating agents. The preferred reagent, 1,1-dibromomethyl-2,2-bis-(acetoxymethyl)-cyclopropane (3), was prepared as shown in FIG. 1. Commercially available diethyl isopropylidene-malonate (4) was converted to bromo derivative 5. Compound 5 was then transformed to a 1:1 mixture of diethyl isopropylidene malonate (4) and diethyl methylene-cyclopropane 1,1-dicarboxylate (6) by a modification of the described procedure. Ullman, E. F., *J. Am. Chem. Soc*. 81:5386-5392 (1959). Compounds 4 and 6 were separated by chromatography on a silica gel column and diethyl methylene-cyclopropane 1,1-di-carboxylate (6) was reduced to 2,2-bis-(hydroxymethyl)methylenecyclopropane (7) by lithium aluminum hydride in ether as described by Dolbier, W. R., et al., *J. Am. Chem. Soc*. 93:3933-3940 (1971). Acetylation with acetic anhydride in pyridine provided 1,1-bis-(acetoxymethyl)methylenecyclopropane (8). Addition of elemental bromine in a suitable solvent such as carbon tetrachloride gave 1,1-dibromomethyl-2,2-bis-(acetoxymethyl)-cyclopropane (3).

Alternately, as shown in FIG. 2, a mixture of diethyl isopropylidene malonate (4) and methylenecyclopropane-2,2-dicarboxylate (6) was reduced with lithium aluminum hydride to give 2-isopropylidenepropane-1,3-diol (9) and 2,2-bis-(hydroxymethylene)methylene-cyclopropane (7). Acetylation provided the corresponding acetates 8+10. Mixtures of compounds 7+9 and 8+10 are not separable by chromatography on a silica gel column. In the next step, addition of bromine on compounds 8+10 was perfomed using pyridinium perbromide in dichloromethane to furnish 1,1-bis(acetoxymethyl)-1,2-dibromo-2,2-dimethyl-ethane (11) and 1,1-dibromomethyl-2,2-bis-(acetoxymethyl)cyclopropane (3) which were separated by chromatography on a silica gel column.

The 1,1-dibromomethyl-2,2-bis-(acetoxymethyl)cyclopropane (3) was used as an alkylating agent in conjunction with an appropriate nucleic acid base adenine (12a) or precursor 2-amino-6-chloropurine (12b) or $N^4$-acetylcytosine (12d). Alkylation effected by potassium carbonate in an organic solvent, e.g., N,N-dimethylformamide, at an elevated temperature, e.g., 100° C., was accompanied by elimination of elements of hydrogen bromide to give the isomeric mixtures of (Z)- and (E)-9-{[2,2-bis-(acetoxymethyl)cyclopropylidene]-methyl}adenines 13a and 14a or (Z)- and (E)-2-amino-6-chloro-9-{[2,2-bis-(acetoxymethyl) cyclopropylidene]-methyl}purines 13b and 14b or (Z)- and (E)-1-{[2,2-bis-(hydroxymethyl)cyclopropylidene]-methyl}cytosines 1e and 2e. In the latter case, N-acetyl and O-acetyl groups were removed by a work-up of the reaction mixture with methanol at an elevated temperature. Deacetylation of intermediates 13a+14a or 13b+14b was performed with potassium carbonate in aqueous methanol to give the (Z)- and (E)-9-{[2,2-bis-(hydroxymethyl)cyclo-propylidene]methyl]}-adenines 1a and 2a or (Z)- and (E)-2-amino-6-chloro-9-{[2,2-bis-(hydroxymethyl)cyclo-propylidene] methyl}purines 1b and 2b which were separated by chromatography on silica gel (FIG. 3).

Because mixture of 1e+2e was not separable by chromatography, it was converted to $N^4$-benzoyl derivatives 15 and 16 by benzoic anhydride in ethanol. This method was used previously for the 1-[(2-hydroxymethyl)cyclo-propylidenemethyl]cytosines. Qiu, Y.-L., et al., *Antiviral Chem. Chemother*. 9:341-352 (1998). The (Z)- and (E)-$N^4$-benzoyl derivatives 15 and 16 were separated by chromatography on silica gel. The individual isomers 15 and 16 were debenzoylated with ammonia in methanol to afford (Z)-1-{[2,2-bis-(hydroxymethyl)cyclopropylidene]methyl}cytosine (1e) and (E)-1-{[2,2-bis-(hydroxymethyl)cyclopropylidene] methyl}cytosine (2e) (FIG. 4).

Figure 6:
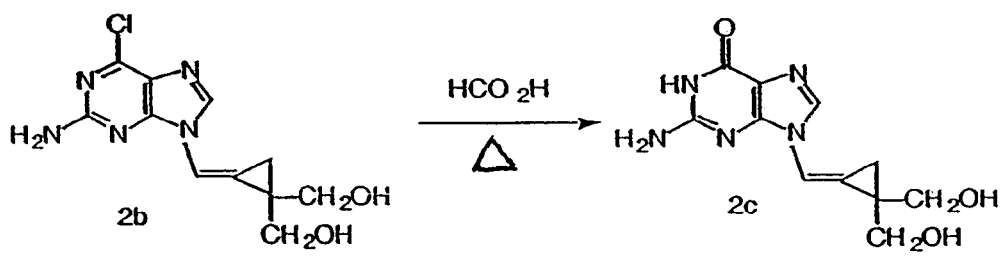
FIG. 6 shows the hydrolysis of (E)-2-amino-6-chloro-9-{[2,2-bis-(hydroxylmethyl)cyclopropylidene]methyl}purine (2b) to (E)-9-{[2,2-bis-(hydroxymethyl)cyclopropylidene]methyl}guanine (2c)

Hydrolysis of separated compounds 1b and 2b with formic acid gave (Z)-9-{[2,2-bis-(hydroxymethyl)cyclopropylidene]methyl}guanine (1c) (FIG. 5) and (E)-9-{[2,2-bis-(hydroxymethyl)cyclopropylidene]methyl}guanine (2c) (FIG. 6).

Figure 7:
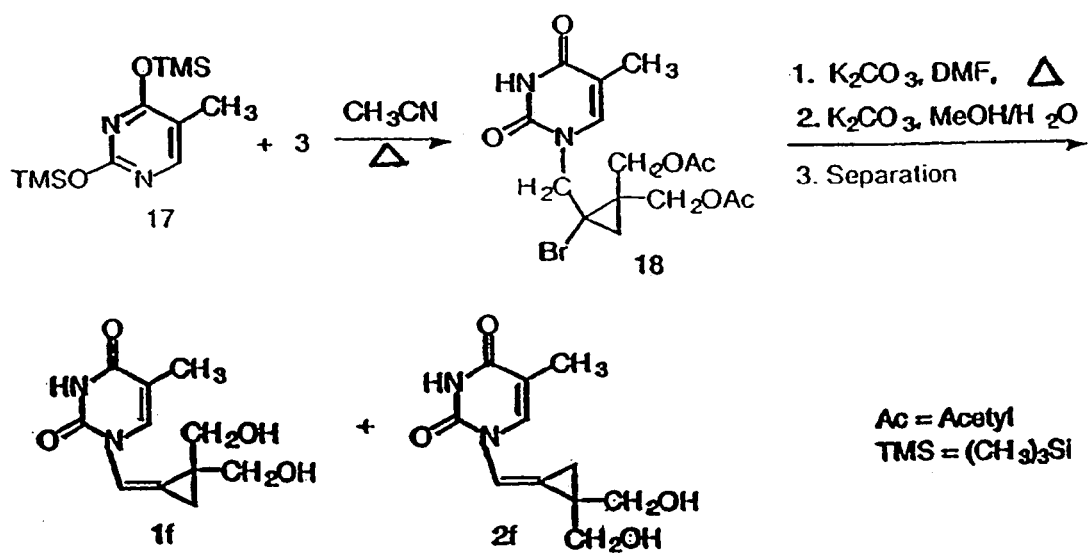
FIG. 7 shows the synthesis of (Z)-1-{[2,2-bis-(hydroxymethyl)cyclo-propylidene]methyl}thymine (1f) and (E)-1-{[2,2-bis-(hydroxymethyl)cyclo-propylidene]methyl}thymine (2f)
Figure 11:
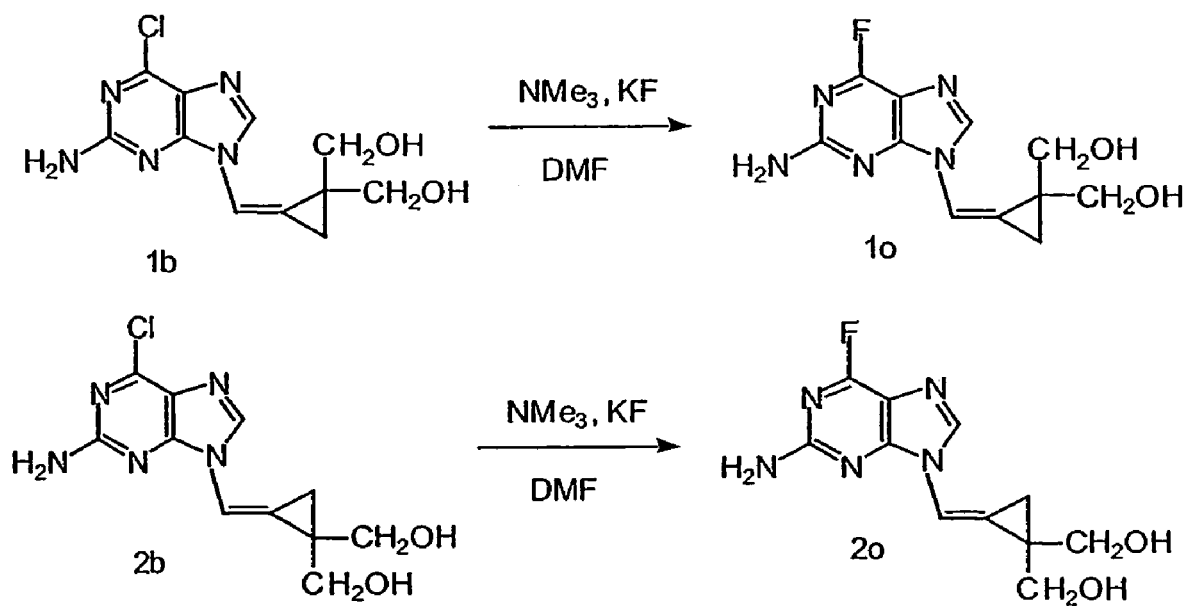
FIG. 11 shows the synthesis of (Z)-2-amino-6-fluoro-9-{[2,2-bis-(hydroxymethyl)cyclopropylidene]methylpurine (1p) and (E)-2-amino-6-fluoro-9-{[2,2-bis-(hydroxylmethyl)cyclopropylidene]methylpurine (2p).

For thymine analogues 1f and 2f a different approach was adopted. The 2,4-bis-(trimethylsilyloxy)-5-methylpyrimidine (17) (prepared as described by Iwai I., et al., In: *Synthetic Procedures in Nucleic Acid Chemistry*, Vol. 1 (Editors Zorbach, W. W. and Tipson, R. S.), John Wiley and Sons, New York, 1968, pp. 338-394) was refluxed with alkylating agent 3 in acetonitrile for a prolonged period of time to give intermediate 18. In a subsequent step, elimination of elements of HBr was performed using potassium carbonate in N,N-dimethylformamide. Finally, deacetylation with potassium carbonate in aqueous methanol afforded (Z)-1-{[2,2-bis-(hydroxymethyl)-cyclopropylidene]methyl}thymine (1f) and (E)-1-{[2,2-bis-(hydroxymethyl)-cyclopropylidene] methyl}thymine (2f) which were separated by chromatography on silica gel (FIG. 7).

Reaction of compound 1b or 2b with methanol and potassium carbonate gave (Z)-2-amino-6-methoxy-9-{[2,2-bis-(hydroxymethyl)cyclopropylidene]-methylpurine (1g) or (E)-2-amino-6-methoxy-9-{[2,2-bis-(hydroxymethyl)cyclopropylidene]methylpurine (2g).

Reaction of compound 1b or 2b with cyclopropylamine gave (Z)-2-amino-6-cyclopropylamino-9-{[2,2-bis-(hydroxymethyl)cyclopropylidene]methylpurine (1h) or (E)-2-amino-6-cyclopropylamino-9-{[2,2-bis-(hydroxymethyl) cyclo-propylidene]methylpurine (2h).

Reaction of compound 1a or 1b with ammonia gave (Z)-2,6-diamino-9-{[2,2-bis-(hydroxymethyl)cyclopropylidene] methylpurine (1o) or (E)-2,6-diamino-9-{[2,2-bis-(hydroxymethyl)cyclopropylidene]methylpurine (2o).

Reaction of compound 1b or 2b with less than stoichiometric amount of trimethylamine and potassium fluoride gave (Z)-2-amino-6-fluoro-9-{[2,2-bis-(hydroxymethyl)cyclo-propylidene]methylpurine (1p) or (E)-2-amino-6-fluoro-9-{[2,2-bis-(hydroxymethyl)cyclo-propylidene]methylpurine (2p).

Compositions within the scope of invention include those comprising a novel compound of the present invention in an effective amount to achieve an intended purpose. Determination of an effective amount and intended purpose is within the skill of the art. Preferred dosages, which are dependent for example, on the severity of the infection and the individual patient's response to the treatment, can range from about 0.01 to about 100 mg/kg of body weight to give a blood concentration ranging from 0.05 µg to about 5 mg per mL of whole blood.

As used herein, the term "pharmaceutically acceptable salts" is intended to mean salts of the compounds of the present invention with pharmaceutically acceptable acids, e.g., inorganic acids such as sulfuric, hydrochloric, phosphoric, etc. or organic acids such as acetic or succinic.

Pharmaceutically acceptable compositions of the present invention may also include suitable carriers comprising excipients and auxiliaries which facilitate processing of the active compounds into preparations which may be used pharmaceutically. Such preparations, preferably those which can be administered orally, include tablets, dragees and capsules. Further preferred preparations are those which can be administered rectally, such as suppositories, as well as suitable solutions for administration by injection or orally, contain about 0.1 to about 99%, preferably 25 to 85%, of the active compound of the present invention, together with the excipient.

The pharmaceutical preparations of the present invention are manufactured in a manner which itself is known, e.g., using the conventional mixing, garnulating, dragee-making, dissolving or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as sugars, e.g., lactose or sucrose, mannitol or sorbitol, cellulose preparations and/or calcium phosphates, e.g., calcium phosphate, (e.g., tricalcium diphosphate or calcium hydrogen phosphate) as well as binders such as starch paste, using, e.g., maize starch, wheat starch, rice starch, potato starch, gelatin, gum tragacanth, methyl cellulose and/or polyvinylpyrrolidone. If desired, disintegrating agents may be added such as the above-mentioned starches, carboxymethyl starch, carboxymethyl cellulose, cross-linked polyvinylpyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated sugar solutions may be used, which may optionally contain gum arabic, talc, polyvinylpyrrolidone, polyethylene glycol and/or titanium dioxide, lacquer solutions and suitable organic solvent or solvent mixtures. In order to produce coatings resistant to gastric juices, solutions of suitable cellulose preparations, such as acetylcellulose phthalate or hydroxypropylmethylcellulose phthalate, are used. Dyestuffs or pigments may be added to the tablets or dragee coatings, e.g., for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules may contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be used.

Possible pharmaceutical preparations which can be used rectally include, e.g., suppositories, which consist of a combination of the active compounds with a suppository base. Suitable suppository bases are, e.g., natural or synthetic triglycerides, paraffin hydrocarbons, polyethylene glycols or higher alkanols. It is also possible to use gelatin rectal capsules which consist of a combination of the active compounds with a base. Possible base materials include, e.g., liquid triglycerides, polyethylene glycols or paraffin hydrocarbons.

Suitable formulations for parenteral administration include aqueous solutions of the active compounds in water-soluble form, e.g., water-soluble salts. In addition, suspension of the active compounds as appropriate oily injection suspensions may be administered. Suitable lipophilic solvents or vehicles include fatty oils, such as sesame oil, or synthetic fatty acid esters, e.g., ethyl oleate or triglycerides. Aqueous injection suspensions may contain substances which increase viscosity of the suspension, such as carboxymethylmethylcellulose, sorbitol and/or dextran. Optionally, the suspension may also contain stabilizers.

Alternately, the active compounds of the present invention may be administered in the form of liposomes, pharmaceutical compositions wherein the active compound is contained either dispersed or variously present in corpuscules consisting of aqueous concentrate layers adherent to hydrophilic lipid layer. The active compound may be present both in the aqueous layer and in the lipidic layer or in non-homogeneous system generally known as lipophilic suspension.

It will be appreciated that the active compounds of the present invention may be administered in combination with known antiviral agents, e.g., acyclovir, ganciclovir, foscarnet, cidofovir, fomivirsen, zidovudine, AZT, ddI, ddC, 3TC and d4T.

The present invention also contemplates prodrugs of the compounds of Formulas 1 and 2. Prodrugs of the antiviral compounds of the present invention may include, e.g., lipophilic phosphate esters or amidates capable of penetrating the cell membrane. Those skilled in the art will appreciate that the aim of prodrugs is to provide effective therapeutic agents for resistant strains of viruses (McGuigan, C., et al., *J. Med. Chem.* 36:1048-1052 (1993)) or activate inactive analogues. Franchetti, P., et al., *J. Med. Chem.* 37:3534-3541 (1994). See also "The Organic Chemistry of Drug Design and Drug Action," Chapter 8, R. B. Silverman, Academic Press (San Diego), 1992.

The following Examples further describe the compounds of the present invention and the synthesis schemes for producing same.

EXAMPLE 1

Synthesis of Diethyl Bromoisopropylidenemalonate
(5)

Diethyl isopropylidenemalonate (4, 50 g, 0.25 mol) was refluxed with stirring with N-bromosuccinimide (44.3 g, 0.25 mol) and dibenzoyl peroxide (1.0 g, 4.1 mmol) in carbon tetrachloride (100 mL) with illumination using Kodak Ectagraphic slide projector lamp ELH (300 Watt) for 1.5 h. The reaction was completed as indicated by a negative starch-iodine test for N-bromosuccinimide. The resulting mixture was diluted with carbon tetrachloride (100 mL) and it was cooled in an ice-bath. The precipitated succinimide was filtered off and the filtrate was evaporated in vacuo at room temperature. The residual pale yellow oil of diethyl bromo-isopropylidene-malonate (5, 71.1 g) was used without purification in the Example 2.

EXAMPLE 2

Diethyl Methylenecyclopropane-2,2-dicarboxylate (6)

Compound 5 (43.4 g, 0.156 mol) from Example 1 was added to a vigorously stirred refluxing solution of potassium tert-butoxide (17.5 g, 0.156 mol) in tert-butyl alcohol (500 mL) under nitrogen. The stirring was continued for 15 min. and the mixture was immediately cooled in an ice bath. Acetic acid was then added, the solid portion was filtered off and thoroughly washed with ether. The filtrate was concentrated in vacuo, diluted with ether and the organic layer was washed several times with water. After drying with magnesium sulfate, the solution was evaporated in vacuo and the residue was distilled, bp. 99-93° C./0.3 torr, yield 14.8 g (47%) of a 1:1 mixture of 4+6. This mixture was chromatographed on a silica gel column using first hexanes-ether (40:1) and then (20:1) to give product 6 (7.3 g, 23%) as a colorless liquid.

$^1$H NMR (CDCl$_3$, 300 MHz) δ 1.24 (t, 6H, J=7.2 Hz, CH$_3$), 2.15 (t, 2H, J=2.4 Hz, H$_3$), 4.17 (q, 4H, J=7.2 Hz, OCH$_2$), 5.53 (t, 1H, J=2.1 Hz) and 5.62 (s, 1H, J=2.6 Hz, C=CH$_2$). $^{13}$C NMR (CDCl$_3$, 75 MHz) ppm 14.21 (CH$_3$), 18.24 (C$_3$), 23.26 (C$_2$), 61.02 (CH$_2$O), 105.20 (=CH$_2$), 130.46 (C$_1$), 167.91 (CO).

EXAMPLE 3

2,2-(Bis-hydroxymethyl)methylenecyclopropane (7)

A solution of diethyl methylenecyclopropane-1,1-dicarboxylate (6, 6.50 g, 32 mmol) from Example 2 in ether (60 mL) was added to a stirred suspension of lithium aluminum hydride (1.90 g, 51 mmol) in ether (50 mL) at such a rate to maintain a gentle reflux. The resultant mixture was refluxed for 15 h. It was then quenched carefully with water (4 mL) and 2 M sodium hydroxide (8 mL). The ether phase was separated and the remaining white precipitate was extracted with ether. Ether from combined organic phases was distilled off using a Vigreux column to give 2,2-bis-(hydroxymethyl)methyl-enecyclopropane (7, 2.84 g, 78% yield) as a residue (colorless oil). The $^1$H-NMR spectrum was identical to that described by Dolbier, W. R., et al., *J. Am. Chem. Soc.* 93:3933-3940 (1971).

EXAMPLE 4

2,2-Bis-(acetoxymethyl)methylenecyclopropane (8)

To a solution of compound 7 (2.65 g, 23 mmol) from Example 3 in pyridine (6 mL) acetic anhydride (13 mL) was added dropwise with stirring at room temperature. The stirring was continued for 16 h. The reaction was quenched with water and the product was extracted with cold (4° C.) pentane (70 mL) at 4° C. The combined organic phase was washed successively with saturated aqueous copper sulfate, 5% hydrochloric acid, aqueous sodium hydrogen carbonate and brine. It was then dried with magnesium sulfate, the solvent was evaporated in vacuo and the residue was chromatographed on a silica gel column (hexanes-ether, 20:1) to give compound 8 as a colorless liquid (4.28 g, 93%).

$^1$H NMR (CDCl$_3$, 300 MHz) δ 1.34 (t, 2H, J=2.1 Hz, H$_3$), 2.07 (s, 6H, CH$_3$), 4.07 (AB, 4H, J$_{AB}$=11.6 Hz, OCH$_2$), 5.46 (t, J=1.8 Hz, 1H) and 5.40 (t, 1H, J=2.7 Hz, C=CH$_2$). $^{13}$C NMR (CDCl$_3$, 75 MHz) ppm 14.32 (C$_3$), 21.14 (CH$_3$), 22.94 (C$_2$), 66.30 (CH$_2$O), 105.96 (=CH$_2$), 134.05 (C$_1$), 171.26 (CO). CI-MS 199 (M+H, 0.27), 57 (100.0).

EXAMPLE 5

1,1-Bis-(acetoxymethyl-2-bromo-2-(bromomethyl)-cyclopropane (3) from 2,2-(bis-acetoxymethyl)methylenecyclopropane (3)

Bromine (3.2 g, 20 mmol) was added dropwise to a solution of compound 8 (3.95 g, 20.0 mmol) from Example 4 in carbon tetrachloride (30 mL) with stirring at 0° C. The stirring was continued for 30 min. The reaction mixture was diluted with ethyl acetate (100 mL) and the organic phase was washed with saturated aqueous solution of sodium thiosulfate and sodium hydrogen carbonate and then with water. After drying with magnesium sulfate, the solvents were evaporated in vacuo and the residue was chromatographed on a silica gel column (hexanes-ethyl acetate, 10:1 and then 5:1) to give compound 3 as a white solid (4.15 g, 58%).

Mp. 56-58° C. $^1$H NMR (CDCl$_3$, 400 MHz) δ 1.33 (d, 1H, J=7.2 Hz) and 1.46 (d, 1H, J=7.2 Hz, H$_2$), 2.08 (s, 3H) and 2.10 (s, 3H, CH$_3$), 3.75 (d, 1H, J=11.2 Hz), 3.96 (d, 1H, J=11.2 Hz), 4.23 (m, 3H) and 4.48 (d, 1H, J=12 Hz, CH$_2$Br+OCH$_2$). $^{13}$C NMR (CDCl$_3$, 100 MHz) ppm 21.12 (C$_2$), 27.22 (CH$_3$), 32.08 (C$_3$), 41.47 (CH$_2$Br), 42.48 (C$_1$), 62.32 and 68.12 (CH$_2$O), 170.96 and 171.01 (CO). CI-MS 361, 359 and 357 (M+H, 21.3, 42.8 and 22.0), 299 (100.0), 277 and 279 (M-Br, 68.2 and 68.0). EI-HRMS calculated for C$_{10}$H$_{14}$$^{79}$Br$_2$O$_4$—Br: 277.0075, found: 277.0074. Calculated for C$_{10}$H$_{14}$Br$_2$O$_4$: C, 33.55; H, 3.94; Br, 44.64. Found: C, 33.75; H, 4.10; Br, 44.80.

EXAMPLE 6

1,1-Bis-(acetoxymethyl-2-bromo-2-(bromomethyl)-cyclopropane (3) from a mixture of compounds 4 and 6

A mixture of compounds 4+6 (2.0 g, 10 mmol) from Example 2 was reduced with lithium aluminum hydride in ether as described in Example 3. The obtained mixture of diols 7 and 9 (866 mg, 76%) was used directly in the next step.

$^1$H NMR (CDCl$_3$, 300 MHz) δ 1.20 (t, 2H, J=2.1 Hz, cyclopropane of compound 7), 1.76 (12H, CH$_3$ of compounds 7+9), 3.65 (AB, 4H, J=10.8 Hz, CH$_2$O of compound 7), 4.27 (s, 4H, CH$_2$O of compound 9), 5.38 (s, 1H) and 5.47 (t, 1H, J=2.1 Hz, CH$_2$=of compound 7).

A mixture of compounds 7+9 (570 mg, 5 mmol) was acetylated using acetic anhydride in pyridine as described in Example 4 to give a 1:1 mixture of acetates 8+10 (915 mg, 92%) which was used directly in the next step.

Compound 10: $^1$H NMR (CDCl$_3$, 400 MHz) δ 1.82 (s, 6H, CH$_3$), 2.03 (s, 6H, CH$_3$ of acetyl), 4.65 (s, 4H, CH$_2$O). $^{13}$C NMR (CDCl$_3$, 100 MHz) ppm 21.06 and 21.20 (CH$_3$), 62.71 (CH$_2$O), 123.12 and 141.19 (C=C), 171.35 (CO).

$^1$H NMR and $^{13}$C NMR of compound 8 were identical with those given in Example 4.

Pyridinium perbromide (1.60 g, 5 mmol) was added to a solution of a mixture of compounds 8+10 (796 mg, 4 mmol) in dichloromethane (50 mL) at 0° C. The reaction mixture was then allowed to stand at room temperature for 15 h. Ethyl acetate (100 mL) was then added and the organic phase was washed with a saturated solution of sodium bicarbonate and sodium thiosulfate followed by water. After drying with sodium sulfate, the solvents were evaporated and the crude product was chromatographed on a silica gel column using hexanes-ethyl acetate (10:1). 1,1-Bis(acetoxymethyl)-1,2-dibromo-2,2-dimethylethane (11) obtained as a colorless liquid was eluted first (529 mg, 37%) followed by compound 3 (white solid, 659 mg, 46%).

Compound 11: $^1$H NMR (CDCl$_3$, 400 MHz) δ 2.05 (s, 6H, CH$_3$ of acetyl), 2.15 (s, 6H, CH$_3$), 4.69 (d, 4H, J=1.6 Hz, CH$_2$O). $^{13}$C NMR (CDCl$_3$, 400 MHz) ppm 21.20 (CH$_3$ of acetyl), 33.06 (CH$_3$), 65.91 (CH$_2$O), 67.08 and 73.33 (C—Br), 170.19 (CO).

Compound 3 was identical with the product described in Example 5.

EXAMPLE 7

(Z)-9-{[2,2-Bis-(acetoxymethyl)cyclopropylidene]methyl}-adenine (13a) and (E)-9-{[2,2-Bis-(acetoxymethyl)cyclopropylidene]-methyl}adenine (14a)

A mixture of adenine (12a, 3.17 g, 2.35 mmol), dibromide 3 (0.84 g, 2.35 mmol) from Example 5 or 6 and flame-dried potassium carbonate (1.95 g, 14.1 mmol) in N,N-dimethylformamide (20 mL) was stirred at 100° C. under nitrogen for 24 h. After cooling, the insoluble portion was filtered off, it was washed with N,N-dimethylformamide and the filtrate was evaporated in vacuo. The residue was chromatographed on a silica gel column using dichloromethane-methanol (20:1) to give a mixture of E- and Z-isomers 13a and 14a (330 mg, 42%) as a white solid.

Mp 155-157° C. UV max (ethanol) 276 nm (ε 7,400), 256 nm (ε 10,800), 228 nm (ε 20,500). $^1$H NMR (CD$_3$SOCD$_3$, 400 MHz) δ 1.61 (s, 2H) and 1.79 (s, 2H, H$_{3'}$), 2.07 (s, 3H) and 2.10 (s, 3H, CH$_3$), 4.10 (d, 2H, J=8 Hz), 4.07 (d, 2H, J=8 Hz), 4.28 (d, 1H, J=11.2 Hz) and 4.43 (d, 1H, J=11.2 Hz, H$_{5'}$), 6.05 (s, 2H) and 6.13 (s, 2H, NH$_2$), 7.56 (s, 1H) and 7.70 (s, 1H, H$_{1'}$), 8.24 (s, 1H, H$_2$, Z-isomer), 8.38 (s, 2H, H$_2$+H$_8$, E-isomer), 8.46 (s, 1H, H$_8$, Z-isomer). $^{13}$C NMR (CD$_3$SOCD$_3$, 100 MHz) ppm 13.27 and 15.84 (C$_{3'}$), 21.03 and 21.15 (CH$_3$), 23.41 and 25.09 (C$_{4'}$), 66.16 and 66.47 (C$_{5'}$), 113.03 (C$_{1'}$), 114.69 and 114.83 (C$_{2'}$ and C$_5$), 136.95 and 137.92 (C$_8$), 149.11 (C$_4$), 153.78 (C$_2$), 155.83 (C$_6$), 170.73 and 171.10 (CO). EI-MS 331 (M, 10.1), 272 (99.5), 230 (46.0), 200 (20.1), 136 (100.0), 135 (30.3), 95 (48.1). EI-HRMS calcd. for C$_{15}$H$_{17}$N$_5$O$_4$: 331.12805, found: 331.12806. Anal. Calcd. for C$_{15}$H$_{17}$N$_5$O$_4$: C, 54.38; H, 5.17; N, 21.14. Found: C, 54.17; H, 5.23; N, 21.29.

EXAMPLE 8

(Z)-9-{[2,2-Bis-(hydroxymethyl)cyclopropylidene]methyl}-adenine (1a) and (E)-9-{[2,2-Bis-(hydroxymethyl)cyclopropylidene]-methyl}adenine (2a)

A mixture of compounds 13a+14a (309 mg, 0.93 mmol) from Example 7 and potassium carbonate (0.83 g, 6 mmol) in methanol-water (9:1, 30 mL) was stirred at room temperature for 12 h whereupon TLC showed a complete reaction. Acetic acid was carefully added and the mixture was evaporated in vacuo. The residue was chromatographed in dichloromethane-methanol (10:1) to give Z- and E-isomers 1a and 2a.

Z-isomer 1a (87 mg, 38%): Mp. 239-242° C. UV max (ethanol) 276 nm (ε 8,200), 262 nm (ε 11,700), 227 nm (ε 25,200). $^1$H NMR (CD$_3$SOCD$_3$, 400 MHz) δ 1.34 (s, 2H, H$_{3'}$), 3.52, 3.68 and 3.53, 3.67 (2AB, $^2$J=11.0 Hz, 4H, H$_{5'}$) ., 5.07 (t, 2H, $^3$J=4.0 Hz OH), 7.37 (s, 1H, H$_{1'}$), 7.36 (s, 2H, NH$_2$), 8.17 (s, 1H, H$_2$), 8.82 (s, 1H, H$_8$). $^{13}$C NMR (CD$_3$SOCD$_3$, 100 MHz) ppm 11.65 (C$_{3'}$), 31.41 (C$_{4'}$), 62.84 (C$_{5'}$), 111.12 (C$_{1'}$), 118.51 (C$_{2'}$), 119.09 (C$_5$), 138.48 (C$_8$), 148.59 (C$_4$), 153.61 (C$_2$), 156.69 (C$_6$). EI-MS 247 (M, 9.1), 230 (14.3), 200 (23.9), 136 (100.0), 135 (56.0), 69 (24.2). EI-HRMS calculated for C$_{11}$H$_{13}$N$_5$O$_2$: 247.1069, found: 247.1069. Calculated for C$_{11}$H$_{13}$N$_5$O$_2$: C, 53.43; H, 5.30; N, 28.32. Found: C, 53.21; H, 5.33; N, 28.57.

E-isomer 2a (66 mg, 29%): Mp 250-252° C. UV max (ethanol) 276 nm (ε 7,100), 260 nm (ε 10,000), 227 nm (ε 21,300). $^1$H NMR (CD$_3$SOCD$_3$, 400 MHz) δ 1.56 (d, 2H, 2H, J=2 Hz, H$_{3'}$), 3.46, 3.52 and 3.48, 3.51 (partially overlapped 2AB, 4H, $^2$J=11.0 and 11.2 Hz, H$_{5'}$)", 4.76 (t, 2H, $^3$J=4.8 Hz, OH), 7.48 (s, 1H, H$_{1'}$), 7.37 (s, 2H, NH$_2$), 8.17 (s, 1H, H$_2$), 8.49 (s, 1H, H$_8$). $^{13}$C NMR (CD$_3$SOCD$_3$, 100 MHz) ppm 14.36 (C$_{3'}$), 29.68 (C$_{4'}$), 63.06 (C$_{5'}$), 110.86 (H$_{1'}$), 119.36 (C$_{2'}$+C$_5$), 137.76 (C$_8$), 148.88 (C$_4$), 153.72 (C$_2$), 156.71 (C$_6$). EI-MS 247 (M, 9.1), 230 (14.3), 200 (23.9), 136 (100.0), 135 (56.0), 69 (24.2), EI-HRMS calculated for C$_{11}$H$_{13}$N$_5$O$_2$: 247.1069, found: 247.1070. Calculated for C$_{11}$H$_{13}$N$_5$O$_2$: C, 53.43; H, 5.30; N, 28.32. Found: C, 53.23; H, 5.48; N, 28.44.

EXAMPLE 9

(Z)-2-Amino-6-chloro-9-{[2,2-bis-(acetoxymethyl)cyclo-propylidene]methyl}purine (13b) and (E)-2-Amino-6-chloro-9-{[2,2-bis-(acetoxymethyl)cyclopropylidene]methyl}purine (14b)

A mixture of 2-amino-6-chloropurine (12b, 393 mg, 2.30 mmol), dibromide 3 (0.83 g, 2.32 mmol) from Example 5 or 6 and flame-dried potassium carbonate (1.90 g, 12.5 mmol) in N,N-dimethylformamide (15 mL) was stirred at 100° C. under nitrogen for 24 h. After cooling, the insoluble portion was filtered off, and it was washed with N,N-dimethylformamide. The filtrate was evaporated in vacuo and the residue was chromatographed on a silica gel column using dichloromethane-methanol (98:2) to give a mixture of Z- and E-isomers 13b and 14b (264 mg, 32%) as a white solid.

Mp. 215-216° C. UV max (ethanol) 311 nm (ε 5,100), 230 nm (ε 21,800), 204 nm (ε 13,700). $^1$H NMR (CD$_3$SOCD$_3$, 400 MHz) δ 1.64 (s, 2H, H$_{3'}$, E-isomer), 1.89 (d, 2.8H, J=2.4 Hz, H$_{3'}$, Z-isomer), 1.94 (s, 6H, CH$_3$, E-isomer), 2.04 (s, 8.4H, CH$_3$, Z-isomer), 4.06-4.15 (m, 2.8H of Z-isomer and 4H of E-isomer, H$_{5'}$) and 4.28 (d, 2.8H, J=11.2 Hz, Z-isomer, H$_{5'}$), 7.02 (s, 2H, NH$_2$, E-isomer), 7.06 (s, 2.8H, NH$_2$, Z-isomer), 7.30 (s, 2.8H, H$_{1'}$, E-isomer), 7.40 (s, 1.4H, H$_{1'}$, Z-isomer), 8.32 (s, 1H, H$_8$, E-isomer), 8.43 (s, 1.4H, H$_8$, Z-isomer). $^{13}$C NMR (CD$_3$SOCD$_3$, 100 MHz) ppm 13.22 and 16.24 (C$_{3'}$), 21.13 and 21.33 (CH$_3$), 23.65 and 25.53 (C$_{4'}$), 65.85 and 66.31 (C$_{5'}$), 112.36 and 112.65 (C$_{1'}$), 117.09 and 117.15 (C$_{2'}$), 123.74 (C$_5$), 140.07 and 140.56 (C$_8$), 150.40 (C$_4$), 153.21 and 153.11 (C$_2$), 160.76 (C$_6$), 170.72 and 170.99 (CO). EI-MS 365 and 367 (M, 9.3 and 3.3), 306 (55.3), 308 (18.3), 170 (72.1), 172 (24.2), 95 (56.6), 94 (33.1), 43 (100.0). EI-HRMS calculated for C$_{15}$H$_{16}^{35}$ClN$_5$O$_4$: 365.0891, found: 365.0888.

EXAMPLE 10

(Z)-2-Amino-6-chloro-9-{[2,2-bis-(hydroxymethyl) cyclo-propylidene]methyl}-purine (1b) and (E)-2-Amino-6-chloro-9-{[2,2-bis-(hydroxymethyl)cyclo-propylidene]-methyl}purine (2b)

A mixture of Z- and E-isomers 13b+14b (260 mg, 0.71 mmol) from Example 9 and potassium carbonate (78 mg, 0.57 mmol) in methanol-water (9:1, 10 mL) was stirred for 30 minutes at room temperature. Acetic acid was carefully added and the mixture was evaporated in vacuo. The residue was chromatographed on a silica gel column in dichloromethane-methanol (10:1) to give Z-isomer 1b (106 mg, 53%) and E-isomer 2b (75 mg, 37%).

Z-isomer 1b: Mp. 207-208° C. UV max (ethanol) 310 nm (ε 7,900), 234 nm (ε 27,800). $^1$H NMR (CD$_3$SOCD$_3$, 400 MHz) δ 1.34 (s, 2H, H$_{3'}$), 3.47, 3.67 and 3.49, 3.66 (2AB, 4H, $^2$J=10.8 and 11.2 Hz, H$_{5'}$), 5.04 (poorly resolved t, 2H, OH), 7.03 (s, 2H, NH$_2$), 7.18 (s, 1H, H$_{1'}$), 8.81 (s, 1H, H$_8$). $^{13}$C NMR (CD$_3$SOCD$_3$, 100 MHz) ppm 11.72 (C$_{3'}$), 31.41 (C$_{4'}$), 62.75 (C$_{5'}$), 110.61 (C$_{1'}$), 119.24 (C$_{2'}$), 123.75 (C$_5$), 140.56 (C$_8$), 150.19 (C$_4$), 152.92 (C$_2$), 160.70 (C$_6$). ESI-MS (MeOH+NaCl) 282 and 284 (M+H, 100.0 and 33.3), 304 and 306 (M+Na, 40.5 and 13.7), 585 and 587 (2M+Na, 32.7 and 24.4). Calculated for C$_{11}$H$_{12}$ClN$_5$O$_2$: C, 46.90; H, 4.29; Cl, 12.59; N, 24.86. Found: C, 47.08; H, 4.35; Cl, 12.38; N, 24.88.

E-isomer 2b: Mp. 230-234° C. (decomp.). UV max (ethanol) 310 nm (ε 8,000), 234 nm (ε 28,800). $^1$H NMR (CD$_3$SOCD$_3$, 400 MHz) δ 1.54 (s, 2H, H$_{3'}$), 3.41, 3.49 and 3.43, 3.47 (2AB, 4H, $^2$J=11.6 and 11.0 Hz, H$_{5'}$), 5.42 (broad s, 2H, OH), 7.02 (s, 2H, NH$_2$), 7.30 (s, 1H, H$_{1'}$), 8.43 (s, 1H, H$_8$). $^{13}$C NMR (CD$_3$SOCD$_3$, 100 MHz) ppm 14.52 (C$_{3'}$), 29.84 (C$_{4'}$), 62.96 (C$_{5'}$), 110.41 (C$_{1'}$), 120.53 (C$_{2'}$), 123.71 (C$_5$), 140.11 (C$_8$), 150.26 (C$_4$), 153.17 (C$_2$), 160.68 (C$_6$). ESI-MS (MeOH+NaCl) 282 and 284 (M+H, 100.0 and 32.1), 304 and 306 (M+Na, 27.4 and 8.9), 585 and 587 (2M+Na, 6.7 and 11.3). Calculated for C$_{11}$H$_{12}$ClN$_5$O$_2$: C, 46.90; H, 4.29; Cl, 12.59; N, 24.86. Found: C, 47.10; H, 4.40; Cl, 12.40; N, 25.04.

EXAMPLE 11

(Z)-9-{[2,2-Bis-(hydroxymethyl)cyclopropylidene]methyl}-guanine (1c)

The solution of the Z-isomer 1b (100 mg, 0.36 mmol) from Example 10 in formic acid (95-97%, 8 mL) was heated at 80° C. with stirring for 4 h. After cooling, the formic acid was evaporated in vacuo and the crude product was dissolved in methanol (30 mL). A precipitated white solid was stirred in methanolic ammonia (20%, 10 mL) at 0° C. for 4 h. After evaporation of volatile components, a suspension of the residue in methanol (100 mL) was refluxed for 2 h. The mixture was kept overnight at 0° C. to give product 1c (83 mg, 89%).

Mp. >300° C. UV max (ethanol) 271 nm (ε 11,500), 231 nm (ε 26,400). $^1$H NMR (CD$_3$SOCD$_3$, 400 MHz) δ 1.29 (s, 2H, H$_{3'}$), 3.48, 3.63 and 3.49, 3.62 (2AB, 4H, $^2$J=10.8 and 11.2 Hz, 4H, $^2$J=10.8 and 11.2, H$_{5'}$), 4.99 (t, 2H, J=5.6 Hz, OH), 6.52 (s, 2H, NH$_2$), 7.07 (s, 1H, H1'), 8.41 (s, 1H, H$_8$), 10.64 (s, 1H, NH). $^{13}$C NMR (CD$_3$SOCD$_3$, 100 MHz) ppm 11.52 (C$_{3'}$), 31.26 (C$_{4'}$), 62.75 (C$_{5'}$), 110.98 (C$_{1'}$), 116.92 (C$_{2'}$), 118.08 (C$_5$), 135.13 (C$_8$), 150.29 (C$_4$), 154.56 (C$_2$), 157.38 (C$_6$). ESI-MS (MeOH+NaCl) 264 (M+H, 5.1), 286 (M+Na, 100.0), 549 (2M+Na, 41.1). Calculated for C$_{11}$H$_{13}$N$_5$O$_3$: C, 50.19; H, 4.98; N, 26.60. Found: C, 50.06; H, 5.09; N, 26.48.

EXAMPLE 12

(E)-9-{[2,2-Bis-(hydroxymethyl)cyclopropylidene]methyl}-guanine (2c)

The procedure described in Example 11 was used for the synthesis of E-isomer 2c (59 mg, 84%) from compound 2b (75 mg, 0.27 mmol) from Example 10.

Mp. >300° C. UV max (ethanol) 271 nm (ε 12,500), 229 nm (ε 31,800). $^1$H NMR (CD$_3$SOCD$_3$, 400 MHz) δ 1.49 (s, 2H, H$_{3'}$), 3.41, 3.48 and 3.43, 3.47 (2AB, 4H, $^2$J=11.6 and 11.0 Hz, H$_{5'}$), 4.76 (t, 2H, $^3$J=5.6 Hz, OH), 6.58 (s, 2H, NH$_2$), 7.21 (s, 1H, H$_{1'}$), 8.03 (s, 1H, H$_8$), 10.77 (s, 1H, NH). $^{13}$C NMR (CD$_3$SOCD$_3$, 100 MHz) ppm 14.26 (C$_{3'}$), 29.51 (C$_{4'}$), 63.04 (C$_{5'}$), 110.78 (C$_{1'}$), 116.90 (C$_{2'}$), 118.93 (C$_5$), 134.27 (C$_8$), 150.52 (C$_4$), 154.60 (C$_2$), 157.44 (C$_6$). ESI-MS (MeOH+NaCl) 264 (M+H, 3.6), 286 (M+Na, 100.0), 549 (2M+Na, 33.0). Calculated for C$_{11}$H$_{13}$N$_5$O$_3$: C, 50.19; H, 4.98; N, 26.60. Found: C, 50.10; H, 5.04; N, 26.89.

EXAMPLE 13

(Z)-1-{[2,2-Bis-(hydroxymethyl)cyclopropylidene]methyl}-cytosine (1e) and (E)-9-{[2,2-Bis-(hydroxymethyl)cyclopropylidene]-methyl}cytosine (2e)

A mixture of N$^4$-acetylcytosine (12d, 1.80 g, 5.0 mmol), dibromide 3 (766 mg, 5.0 mmol) from Example 5 or 6 and flame-dried potassium carbonate (4.75 g, 30 mmol) in N,N-dimethylformamide (100 mL) was stirred at 100° C. under nitrogen for 12 h. The mixture was cooled to 50° C. and methanol (5 mL) was added with stirring which was continued for 5 h. After cooling, the insoluble portion was filtered off and it was washed with N,N-dimethylformamide. The filtrate was evaporated in vacuo and the residue was chromatographed on a silica gel column in dichloromethane-methanol (20:1 and then 4:1) to give a mixture of products 1e+2e (680 mg, 61%) as a white solid in a ratio of 1:1.4.

$^1$H NMR (CD$_3$SOCD$_3$, 400 MHz) d 1.14 (s, 2H, H$_{3'}$, Z-isomer), 1.40 (s, 2.8H, H$_{3'}$, E-isomer), 3.36-3.47 (m, 7.8H, H$_{5'}$), 4.70 (s, 2.8, OH, E-isomer), 4.95 (s, 2H, OH, Z-isomer), 5.78 (d, 1H, J=5.6 Hz, H$_5$, Z-isomer), 5.85 (d, 1.4H, J=6.0 Hz, H$_5$, E-isomer), 7.31 (s, 1H, H$_{1'}$, Z-isomer), 7.38 (s, 1.4H, H$_{1'}$, E-isomer), 7.45 (s, 2.8H, NH$_2$, E-isomer), 7.97 (d, 1.4H, J=6.0 Hz, H$_6$, E-isomer), 8.24 (d, 1H, J=6.4 Hz, H$_6$, Z-isomer). $^{13}$C NMR (CD$_3$SOCD$_3$, 100 MHz) ppm 10.72 (C$_{3'}$, Z-isomer), 13.64 (C$_{3'}$, E-isomer), 27.46 (C$_{4'}$, E-isomer), 31.08 (C$_{4'}$, Z-isomer), 62.99 (C$_{5'}$, Z-isomer), 63.17 (C$_{5'}$, E-isomer), 95.52 (C$_5$, Z-isomer), 95.79 (C$_5$, E-isomer), 114.69 (C$_{1'}$, Z-isomer), 115.32 (C$_{1'}$, E-isomer), 115.70 (C$_{2'}$, E-isomer), 116.56 (C$_{2'}$, Z-isomer), 140.77 (C$_6$, E-isomer), 141.12 (C$_6$, Z-isomer), 154.66 (C$_4$, Z-isomer), 154.87 (C$_4$, E-isomer), 166.07 (C$_2$).

EXAMPLE 14

(Z)- and (E)-N$^4$-Benzoyl-1-{[2,2-bis-(hydroxymethyl)-cyclopropylidene]methyl}cytosine (15) and (16)

A mixture of 1e+2e from Example 13 was dissolved in refluxing ethanol (100 mL). Benzoic anhydride (689 mg, 3.05 mmol) was added with stirring into a hot solution and the refluxing was continued for 1 h. Five more portions of benzoic anhydride (689 mg, 3.05 mmol each) were added every hour. After cooling, the solvent was evaporated and the crude product was chromatographed on a silica gel column in dichloromethane-methanol (20:1) to give Z-isomer 15 (380 mg, 38%) and E-isomer 16 (350 mg, 35%) as white solids.

Z-isomer 15: Mp 222-223° C. UV max (ethanol) 329 nm ($\epsilon$ 14,200), 270 nm ($\epsilon$ 19,200), 203 nm ($\epsilon$ 23,900). $^1$H NMR (CD$_3$SOCD$_3$, 400 MHz) δ 1.28 (s, 2H, H$_{3'}$), 3.46, 3.66 and 3.48, 3.64 (2AB, 4H, J=10.8 and 11.4 Hz), 4.99 (s, 2H, OH), 7.32 (d, J=8 Hz, 1H), 7.39-7.50 (m, 3H, H$_{1'}$+H$_{meta}$'s of benzoyl), 7.64 (m, 3H), 7.60 (t, 1H, J=8 Hz, H$_{para}$ of benzoyl), 7.98 (d, 2H, J=8 Hz, H$_{ortho}$'s of benzoyl), 8.70 (d, J=7.2 Hz, 11H, H$_6$), 11.30 (s, 1H, NH). $^{13}$C NMR (CD$_3$SOCD$_3$, 100 MHz) ppm 10.96 (C$_{3'}$), 31.53 (C$_{4'}$), 62.86 (C$_{5'}$), 97.35 (C$_5$), 116.41 (C$_{1'}$), 120.17 (C$_{2'}$), 129.94 (C$_{ortho}$ of benzoyl), 129.18 (C$_{meta}$ of benzoyl), 133.46 (C$_{para}$ of benzoyl), 145.24 (C$_6$), 153.99 (C$_4$), 163.64 (C$_2$), 168.25 (CO of benzoyl). ESI-MS (MeOH+NaCl) 328 (M+H, 100.0), 350 (M+Na, 71.9), 677 (2M+Na, 52.1). Calculated for C$_{17}$H$_{17}$N$_3$O$_4$: C, 62.38; H, 5.23 N. 12.84. Found: C, 62.50; H, 5.41; N, 13.02.

E-isomer 16: Mp 221-223° C. UV max (ethanol) 329 nm ($\epsilon$ 14,200), 269 nm ($\epsilon$ 18,900), 203 nm ($\epsilon$ 23,400). $^1$H NMR (CD$_3$SOCD$_3$, 400 MHz) δ 1.52 (s, 2H), 3.44, 3.50 and 3.45, 3.48 (2AB, 4H, $^2$J=11.2 and 11.4 Hz, H$_{5'}$), 7.45-7.51 (m, 3H, H$_{1'}$+H$_{meta}$'s of benzoyl), 7.60 (d, 1H, J=7.2 Hz, H$_{para}$ of benzoyl), 7.99 (d, 2H, J=7.2 Hz, H$_{ortho}$'s of benzoyl), 8.46 (d, 1H, J=7.2 Hz, H$_6$), 11.33 (s, 1H, NH). $^{13}$C NMR (CD$_3$SOCD$_3$, 100 MHz) ppm 13.66 (C$_{3'}$), 28.16 (C$_{4'}$), 62.96 (C$_{5'}$), 97.66 (C$_5$), 115.46 (C$_{1'}$), 120.77 (C$_{2'}$), 129.13 (C$_{ortho}$ of benzoyl), 129.18 (C$_{meta}$ of benzoyl), 133.46 (C$_{para}$ of benzoyl), 133.75 (C$_{ipso}$ of benzoyl), 145.09 (C$_6$), 154.33 (C$_4$), 163.72 (C$_2$), 167.97 (CO of benzoyl). ESI-MS (MeOH+NaCl) 328 (M+H, 100.0), 350 (M+Na, 97.6), 677 (2M+Na, 100.0). EI-HRMS calculated for C$_{17}$H$_{17}$N$_3$O$_4$: 327.1219, found: 327.1221. Calculated for C$_{17}$H$_{17}$N$_3$O$_4$: C, 62.38; H, 5.23; N, 12.84. Found: C, 62.14; H, 5.30; N, 12.63.

EXAMPLE 15

(Z)-1-{[2,2-Bis-(hydroxymethyl)cyclopropylidene]methyl}-cytosine (1e)

The Z-isomer 15 (297 mg, 0.91 mmol) from Example 14 was stirred in methanolic ammonia (20%, 30 mL) at room temperature for 12 h. The solvent was evaporated and the crude product was chromatographed on a silica gel column in dichloromethane-methanol (4:1) to give the Z-isomer 1e (174 mg, 86%) as a white solid.

Mp 250-253° C. UV max (ethanol) 297 nm ($\epsilon$ 11,900), 230 nm ($\epsilon$ 12,700), 206 ($\epsilon$ 13,700). $^1$H NMR (CD$_3$SOCD$_3$, 400 MHz) δ 1.14 (s, 2H, H$_{3'}$), 3.34 and 3.57 (AB, 4H, $^2$J=11.0 Hz, H$_{5'}$), 5.02 (broad s, 2H, OH, 5.82 (d, 1H, J=7.2 Hz, H$_5$), 7.31 (s, 1H, H$_{1'}$), 7.43 and 7.55 (2s, 2H, NH$_2$), 8.27 (d, 1H, J=Hz, H$_6$). $^{13}$C NMR (CD$_3$SOCD$_3$, 100 MHz) ppm 10.75 (C$_{3'}$), 31.07 (C$_{4'}$), 63.03 (C$_{5'}$), 95.69 (C$_5$), 114.95 (C$_{1'}$), 116.52 (C$_{2'}$), 141.20 (C$_6$), 154.85 (C$_4$), 166.12 (C$_2$). ESI-MS (MeOH+NaCl) 224 (M+H, 2.7), 246 (M+Na, 100.0), 469 (2M+Na, 81.0). EI-HRMS calculated for C$_{10}$H$_{13}$N$_3$O$_3$: 223.0957, found: 223.0953. Calculated for C$_{10}$H$_{13}$N$_3$O$_3$: C, 53.80; H, 5.87; N, 18.82. Found: C, 53.71; H, 6.00; N, 18.75.

EXAMPLE 16

(E)-9-{[2,2-Bis-(hydroxymethyl)cyclopropylidene]methyl}-cytosine (2e)

The E-isomer 16 (263 mg, 0.80 mmol) from Example 14 was debenzoylated using the procedure described in Example 15 to give compound 2e (149 mg, 83%).

Mp 249-251° C. UV max (ethanol) 298 nm ($\epsilon$ 12,200), 229 nm ($\epsilon$ 12,300), 206 nm ($\epsilon$ 11,900). $^1$H NMR (CD$_3$SOCD$_3$, 400 MHz) δ 1.39 (s, 2H, H$_{3'}$), 3.37, 3.42 and 3.37, 3.41 (2AB, 4H, $^2$J=10.6 and 11.2 Hz, H$_{5'}$), 4.78 poorly resolved t, 2H, OH), 5.89 (d, 1H, J=8 Hz, H$_5$), 7.38 (s, 1H, H$_{1'}$), 7.40 and 7.57 (2s, 2H, NH$_2$), 7.96 (d, 1H, J=7.4 Hz, H$_6$). $^{13}$C NMR (CD$_3$SOCD$_3$, 100 MHz) ppm 13.68 (C$_{3'}$), 27.47 (C$_{4'}$), 63.18 (C$_{5'}$), 95.92 (C$_5$), 115.46 (C$_{1'}$), 115.66 (C$_{2'}$), 140.77 (C$_6$), 154.98 (C$_4$), 166.09 (C$_2$). EI-MS (MeOH+NaCl) 224 (M+H, 2.7), 246 (M+Na, 100.0), 469 (2M+Na, 81.0). Calculated for C$_{10}$H$_{13}$N$_3$O$_3$: C, 53.80; H, 5.87; N, 18.82. Found: C, 54.01; H, 6.02; N, 18.72.

EXAMPLE 17

1-{[1-Bromo-2,2-bis-(acetoxymethyl)cyclopropyl]methyl}-thymine (18)

A mixture of 2,4-bis-(trimethylsilyloxy)-5-methylpyrimidine (17, 680 mg, 2.50 mmol) and dibromoester 3 (0.90 g, 2.5 mmol) from Example 5 or 6 was refluxed in acetonitrile (20 mL) for 148 h. After cooling, ethanol (20 mL) was added and solvents were evaporated. The residue was triturated with dichloromethane (50 mL), the insoluble portion was filtered off using a bed of silica gel which was then washed with dichloromethane-methanol (30:1). The combined filtrate and washings were evaporated. The crude product was chromatographed on a silica gel column in dichloromethane-methanol starting from 100% dichloromethane and increasing the amount of methanol to 40:1 to give compound 18 (750 mg, 74.4%) as a white solid.

Mp 197-198° C. UV max (ethanol) 268 nm ($\epsilon$ 10,400), 210 nm ($\epsilon$ 8,900). $^1$H NMR (CD$_3$SOCD$_3$, 400 MHz) δ 1.38 (d, 1H, J=7.2 Hz, 1H) and 1.72 (d, 1H, J=7.2 Hz, H$_{3'}$), 1.78 (s, 3H, 5-CH$_3$), 2.02 (s, 3H) and 2.04 (s, 3H, CH$_3$ of acetyl), 4.10-4.17 (m, 3H) and 4.30-4.47 (m, 3H, H$_{1'}$+H$_{5'}$), 7.54 (s, 1H, H$_6$), 11.35 (s, 1H, NH). $^{13}$C NMR (CD$_3$SOCD$_3$, 100 MHz) ppm 12.76 (5-CH$_3$), 21.29 (C$_{3'}$), 24.99 (C$_{4'}$), 28.55 (CH3 of acetyl), 43.25 (C$_{2'}$), 52.47 (C$_{1'}$), 64.13 and 68.75 (C$_{5'}$), 109.18 (C$_5$), 141.60 (C$_6$), 151.82 (C$_2$), 164.79 (C$_4$), 170.78 and 170.86 (CO of acetyl). EI-MS 405 and 403 (M, 4.4 and 4.4), 263 (6.2), 126 (10.9), 95 (9.4), 55 (10.6), 43 (100.0). EI-HRMS calculated for C$_{15}$H$_{19}$$^{79}$BrN$_2$O$_6$: 402.0426, found: 402.0427. Calculated for C$_{15}$H$_{19}$BrN$_2$O$_6$: C, 44.68; H, 4.75; Br, 19.82; N, 6.95. Found: C, 44.57; H, 4.89; Br, 19.83; N, 6.86.

EXAMPLE 18

(Z)-1-{[2,2-Bis-(hydroxymethyl)cyclopropylidene]methyl}-thymine (1f) and (E)-9-{[2,2-Bis-(hydroxymethyl)cyclopropylidene]-methyl}thymine (2f)

A mixture of compound 18 (0.60 g, 1.49 mmol) from Example 17 and flame-dried potassium carbonate (616 mg, 4.47 mmol) in N,N-dimethylformamide (50 mL) was stirred at 100° C. under nitrogen for 3 h. After cooling, methanol-water (9:1, 10 mL) was added with stirring which was continued at room temperature for 1 h. The insoluble portion was filtered off and it was washed with N,N-dimethylformamide. The filtrate was evaporated in vacuo and the residue was chromatographed on a silica gel column which was first eluted with ethyl acetate and then dichloromethane-methanol (20:1) to give the Z-isomer 1f (70 mg, 38%) and E-isomer 2f (65 mg, 36%) as white solids.

Z-isomer 1f: Mp 177-179° C. UV max (ethanol) 289 nm ($\epsilon$ 11,700), 232 nm ($\epsilon$ 12,800). $^1$H NMR (CD$_3$SOCD$_3$, 400 MHz) δ 1.17 (s, 2H, H$_{3'}$), 1.76 (s, 3H, 5-CH$_3$), 3.40, 3.61 and 3.41, 3.60 (2AB, 4H, $^2$J=10.6 and 11.2 Hz, H$_{5'}$), 4.99 (t, J=6.0 Hz, 2H, OH), 7.17 (s, 1H, H$_{1'}$), 8.32 (s, 1H, H$_6$), 11.42 (s, 1H, NH). $^{13}$C NMR (CD$_3$SOCD$_3$, 100 MHz) ppm 10.86 (C$_{3'}$), 12.68 (5-CH$_3$), 31.18 (C$_{4'}$), 62.96 (C$_{5'}$), 111.39 (C$_{1'}$), 114.40 (C$_{2'}$), 115.19 (C$_5$), 136.82 (C$_6$), 149.99 (C$_2$), 164.41 (C$_4$). EI-MS 238 (M, 10.4), 221 (6.6), 127 (40.7), 126 (10.9), 113 (100.0), 83 (68.3), 55 (26.6). EI-HRMS calculated for C$_{11}$H$_{14}$N$_2$O$_4$: 238.0954, found: 238.0953. Calculated for C$_{11}$H$_{14}$N$_2$O$_4$: C, 55.46; H, 5.92; N, 11.76. Found: C, 55.47; H, 5.96; N, 11.90.

E-isomer 2f: Mp 197-199° C. UV max (EtOH) 289 nm ($\epsilon$ 11,000), 233 nm ($\epsilon$ 12,100). $^1$H NMR (CD$_3$SOCD$_3$, 400 MHz) δ 1.47 (d, 2H, J=1.6 Hz), 1.82 (s, 3H, 5-CH$_3$), 3.38, 3.45 and 3.40, 3.43 (2AB, 4H, $^2$J=11.2 and 11.4 Hz, H$_{5'}$), 4.66 (t, 2H, J=5.6 Hz, OH), 7.25 (s, 1H, H$_{1'}$), 7.82 (s, 1H, H$_6$), 11.46 (s, 1H, NH). $^{13}$C NMR (CD$_3$SOCD$_3$, 100 MHz) ppm 12.82 (C$_{3'}$), 13.94 (5-CH$_3$), 27.83 (C$_{4'}$), 63.09 (C$_{5'}$), 110.86 (C$_{1'}$), 113.77 (C$_{2'}$), 116.33 (C$_5$), 136.12 (C$_6$), 150.20 (C$_2$), 164.38 (C$_4$). EI-MS 238 (M, 12.8), 221 (27.5), 130 (17.7), 127 (100.0), 117 (19.4), 112 (74.9), 83 (49.3). EI-HRMS calculated for C$_{11}$H$_{14}$N$_2$O$_4$: 238.0954, found: 238.0955. Calculated for C$_{11}$H$_{14}$N$_2$O$_4$: C, 55.46; H, 5.92; N, 11.76. Found: C, 55.62; H, 6.01; N, 11.88.

EXAMPLE 19

(Z)-2-amino-6-methoxy-{[2,2-Bis-(hydroxymethyl)cyclo-propylidene]methyl}purine (1g)

A solution of compound 1b (95 mg, 0.34 mmol) from Example 10 and potassium carbonate (94 mg, 0.68 mmol) in methanol (15 mL) was refluxed for 4 h. After cooling, the solvent was evaporated and the residue was chromatographed on a silica gel column using dichloromethane-methanol (10:1) to give the title compound 1g (86 mg, 91%).

Mp. 188-189° C. UV max (ethanol) 278 nm ($\epsilon$ 10,400), 225 nm ($\epsilon$ 26,900), 203 nm ($\epsilon$ 17,200). $^1$H NMR (CD$_3$SOCD$_3$, 400 MHz) δ 1.31 (s, 2H, H$_{3'}$), 3.49, 3.66 and 3.51, 3.65 (2AB, 4H, $^2$J=11.0 and 10.4 Hz, H$_{5'}$), 3.95 (s, 3H, OCH$_3$), 5.03 (t, 1H, $^3$J=4.8 Hz), 6.53 (s, 2H, NH$_2$), 7.19 (s, 1H, H$_{1'}$), 8.56 (s, 1H, H$_8$). $^{13}$C NMR (CD$_3$SOCD$_3$, 100 MHz) ppm 11.62 (C$_{3'}$), 31.30 (C$_{4'}$), 53.96 (OCH$_3$), 62.83 (C$_{5'}$), 110.96 (C$_{1'}$), 114.12 (C$_{2'}$), 117.70 (C$_5$), 137.27 (C$_8$), 153.09 (C$_4$), 160.77 (C$_2$), 161.37 (C$_6$). EI-MS 277 (M, 23.1), 166 (100.0). Calculated for C$_{12}$H$_{15}$N$_5$O$_3$: C, 51.98; H, 5.45; N, 25.26. Found: C, 52.08; H, 5.16; N, 25.18.

EXAMPLE 20

(E)-2-Amino-6-methoxy-9-{[2,2-bis-(hydroxymethyl)cyclo-propylidene]methyl}purine (2g)

A mixture of compound 2b (140 mg, 0.50 mmol) from Example 10 and potassium carbonate (276 mg, 2.0 mmol) in methanol (20 mL) was refluxed for 2 h. The work-up followed the procedure for the Z-isomer 1g described in Example 19 to give compound 2g (127 mg, 92%).

Mp. 179-180° C. UV max (ethanol) 279 nm ($\epsilon$ 10,000), 224 nm ($\epsilon$ 28,200), 201 nm ($\epsilon$ 21,200). $^1$H NMR (CD$_3$SOCD$_3$, 400 MHz) δ 1.51 (s, 2H, H$_{3'}$), 3.43, 3.50 and 3.45, 3.49 (2AB, 4H, $^2$J=11.2 and 11.0 Hz, H$_{5'}$), 3.95 (s, 3H, OCH$_3$), 4.71 (t, $^3$J=5.6 Hz, 2H, OH), 6.51 (s, 2H, H$_2$), 7.31 (s, 1H, H$_{1'}$), 8.20 (s, 1H, H$_8$). $^{13}$C NMR (CD$_3$SOCD$_3$, 100 MHz) ppm 14.34 (C$_{3'}$), 29.56 (C$_{4'}$), 53.9 (OCH$_3$), 63.10 (C$_{5'}$), 110.78 (C$_{1'}$), 114.11 (C$_{2'}$), 118.60 (C$_5$), 136.54 (C$_8$), 153.35 (C$_4$), 160.78 (C$_2$), 161.37 (C$_6$). EI-MS 277 (M, 3.0), 260 (M-OH, 8.7), 179 (100.0). EI-HRMS calcd. for C$_{12}$H$_{15}$N$_5$O$_3$: 277.1175, found: 277.1174. Calculated for C$_{12}$H$_{15}$N$_5$O$_3$: C, 51.98; H, 5.45; N, 25.26. Found: C, 52.21; H, 5.32; N, 25.45.

EXAMPLE 21

(Z)-2-Amino-6-cyclopropylamino-9-{[2,2-bis-(hydroxymethyl)-cyclopropylidene]methyl}purine (1h)

A solution of compound 1b (140 mg, 0.5 mmol) from Example 10 and cyclopropylamine (0.14 mL, 1.0 mmol) was stirred at room temperature for 40 h. After cooling, the volatile components were evaporated and the residue was chromatographed using CH$_2$Cl$_2$: methanol (10:1) to give compound 1h (139 mg, 92%).

Mp. 195-196° C. UV max (ethanol) 286 nm (p 16,600), 224 nm ($\epsilon$ 40,200). $^1$H NMR (CD$_3$SOCD$_3$, 300 MHz) δ 0.54-0.57 (m, 2H) and 0.62-0.66 (m, 2H, CH$_2$ of cyclopropyl), 1.28 (d, 2H, J=2.1 Hz, H$_{3'}$), 3.01 (s, 1H, CH of cyclopropyl), 3.49, 3.63 and 3.51, 3.62 (2AB, 4H, $^2$J=11.0 and 10.8 Hz, H$_{5'}$), 5.00 (t, 2H, $^3$J=4.8 Hz, OH), 5.94 (s, 2H, 2-NH$_2$), 7.16 (s, 1H, H$_{1'}$), 7.36 (poorly resolved d, 1H, 6-NH), 8.40 (s, 1H, H$_8$). $^{13}$C NMR (CD$_3$SOCD$_3$, 75 MHz) ppm 7.19 (CH$_2$ of cyclopropyl), 11.61 (C$_{3'}$), 24.61 (CH of cyclopropyl), 31.25 (C$_{4'}$), 62.89 (C$_{5'}$), 111.22 (C$_{1'}$), 113.71 (C$_{2'}$), 116.77 (C$_5$), 135.00 (C$_8$), 156.59 (C$_2$), 161.07 (C$_6$). ESI-MS 303 (M+H), 325 (M+Na), 605 (2M+Na), 627 (2M+Na). Calculated for C$_{14}$H$_{18}$N$_5$O$_2$: C, 55.62; H, 6.00; N, 27.80. Found: C, 55.79; H, 5.86; N, 27.80.

EXAMPLE 22

(E)-2-Amino-6-cyclopropylamino-9-{[2,2-bis-(hydroxymethyl)-cyclopropylidene]methyl}purine (2h)

The procedure described for the Z-isomer 1h in Example 21 was followed with the E-isomer 2b and cyclopropylamine (0.70 mL, 5 mmol, 50° C., 20 h) to give compound 2h (130 mg, 86%).

Mp. 164-165° C. UV max (ethanol) 286 nm ($\epsilon$ 16,300), 224 nm ($\epsilon$ 37,900). $^1$H NMR (CD$_3$SOCD$_3$, 300 MHz) δ 0.57 (s, 2H) and 0.61-0.66 (m, 2H, CH$_2$ of cyclopropyl), 1.48 (s, 2H, H$_{3'}$), 3.00 (bs, 1H, CH of cyclopropyl), 3.43, 3.50 and 3.45, 3.48 (2AB, 4H, $^2$J=11.4 and 11.0, H$_{5'}$), 4.71 (t, $^3$J=5.9 Hz, 2H, OH), 5.91 (s, 2H, 2-NH$_2$), 7.30 (poorly resolved t, 1H, H$_{1'}$), 7.41 (bs, 1H, 6-NH), 8.04 (s, 1H, H$_8$). $^{13}$C NMR ppm 7.1 (CH$_2$ of cyclopropyl), 14.3 (C$_{3'}$), 24.5 (CH of cyclopropyl), 29.4 (C$_{4'}$), 63.2 (C$_{5'}$), 111.0 (C$_{1'}$), 113.67 (C$_{2'}$), 117.34 (C$_5$), 133.9 (C$_8$), 150.7 (C$_4$), 156.6 (C$_2$), 161.2 (C$_6$). EI-MS 302 (M, 92.2), 285 (M-OH, 35.0), 191 (100.0). EI-HRMS calcd. for C$_{14}$H$_{18}$N$_5$O$_2$: 302.1491, found: 302.1491. Calculated for C$_{14}$H$_{18}$N$_5$O$_2$: C, 55.62; H, 6.00; N, 27.80. Found: C, 55.52; H, 5.96; N, 27.69.

EXAMPLE 23

(Z)-2,6-Diamino-9-{[2,2-bis-(hydroxymethyl)cyclo-propylidene]-methyl}-purine (1o)

A mixture of compound 1b (140 mg, 0.5 mmol) from Example 10 and $NH_3$ in methanol (saturated at 0° C., 60 mL) was heated in a stainless steel bomb at 100° C. for 20 h. After cooling, the volatile components were evaporated and the residue was chromatographed on silica gel using dichloromethane-methanol (4:1) to give the title compound 1o (111 mg, 85%).

Mp. 249-250° C. UV max (ethanol) 280 nm (ε 13,400), 220 nm (ε 35,500). $^1$H NMR ($CD_3SOCD_3$, 400 MHz) δ 1.27 (s, 2H, $H_{3'}$), 3.49, 3.62 and 3.50, 3.61 (2AB, 4H, $^2J$=10.8 and 10.4 Hz, $H_{5'}$), 5.03 (t, 2H, $^3J$=4.8 Hz, OH), 5.85 (s, 2H, 2-$NH_2$), 6.74 (s, 2H, 6-$NH_2$), 7.13 (s, 1H, $H_{1'}$), 8.39 (s, 1h, $H_8$). $^{13}$C NMR ($CD_3SOCD_3$, 100 MHz) ppm 11.61 ($C_{3'}$), 31.28 ($C_{4'}$), 62.89 ($C_{5'}$), 111.24 ($C_{1'}$), 113.47 ($C_{2'}$), 116.65 ($C_5$), 135.16 ($C_8$), 150.90 ($C_4$), 156.82 ($C_2$), 161.21 ($C_6$). EI-MS 262 (M, 19.6), 150 (100.0). EI-HRMS calcd. for $C_{11}H_{14}N_6O_2$: 262.1178, found 262.1175. Calculated for $C_{11}H_{14}N_6O_2$: C, 50.38; H, 5.38; N, 32.04. Found: C, 50.49; H, 5.12; N, 32.24.

EXAMPLE 24

(E)-2,6-Diamino-9-{[2,2-bis-(hydroxymethyl)cyclo-propylidene]-methyl}purine (2o)

The procedure described for the Z-isomer 1o in Example 23 was performed on a 0.34 mmol scale of compound 2b to give the E-isomer 2o (72 mg, 81%).

Mp. 219-220° C. UV max (ethanol) 280 nm (ε 13,700), 220 nm (ε 42,700). $^1$H NMR 1.48 (d, 2H, J=2.4 Hz, $H_{3'}$), 3.43, 3.50 and 3.45, 3.48 (2AB, 4H, $^2J$=11 Hz, $H_{5'}$), 4.68 (t, 2H, $^3J$=3.0 Hz, OH), 5.85 (s, 2H, 2-$NH_2$), 6.77 (s, 2H, $NH_2$), 7.27 (t, 1H, J=2.4 Hz, $H_{1'}$), 8.04 (s, 1H, $H_8$). $^{13}$C NMR ($CD_3SOCD_3$, 100 MHz) ppm 14.27 ($C_{3'}$), 29.41 ($C_{4'}$), 63.19 ($C_{5'}$), 110.99 ($C_{1'}$), 113.42 ($C_{2'}$), 117.42 ($C_5$), 134.22 ($C_8$), 151.20 ($C_4$), 156.83 ($C_2$), 161.25 ($C_6$). EI-MS 262 (M, 26.9), 151 (100.0). EI-HRMS calcd. for $C_{11}H_{14}N_6O_2$: 262.1178, found 262.1172. Calculated for $C_{11}H_{14}N_6O_2$: C, 50.38; H, 5.38; N, 32.04. Found: C, 50.51; H, 5.13; N, 32.30.

EXAMPLE 25

(Z)-2-Amino-6-fluoro-9-{[2,2-bis-hydroxymethyl)cyclo-propylidene]methyl}-purine (1p)

A mixture of the Z-isomer 1b (140 mg, 0.5 mmol) from Example 10, 1 M solution of trimethylamine in N,N-dimethylformamide (0.21 mL, 0.21 mmol) and potassium fluoride (400 mg, 6.9 mmol, dried in vacuo at room temperature/0.05-0.07 torr for 12 h) in N,N-dimethylformamide (5 mL) was vigorously stirred at room temperature for 24 h. The solids were filtered off, they were washed with DMF and the filtrate was evaporated in vacuo. The crude product was chromatographed on silica gel using ethyl acetate-methanol (50:1 to 30:1) to give the title compound 1p (113 mg, 85%).

Mp. 185-188° C. UV max (ethanol) 289 nm (ε 8,400), 268 nm (ε 8,700), 299 nm (ε 37,000). $^1$H NMR ($CD_3SOCD_3$, 400 MHz) δ 1.34 (s, 2H, $H_{3'}$), 3.35, 3.67 and 3.49, 3.66 (2AB, 4H, $J_{AB}$=10.2 Hz), 5.02 (poorly resolved t, 2H, OH), 7.01 (s, 2H, $NH_2$), 7.20 (s, 1H, $H_{1'}$), 8.77 (s, 1H). $^{13}$C NMR 11.67 ppm ($C_{3'}$), 31.40 ($C_{4'}$), 62.78 ($C_{5'}$), 110.78 ($C_{1'}$), 111.86 ($C_5$, d, $J_{C,F}$=31.3 Hz), 119.04 ($C_{2'}$), 140.22 ($C_8$), 156.37 ($C_4$, $J_{C,F}$=12.0 Hz), 159.87 ($C_6$, d, $^1J_{C,F}$=250.7 Hz), 160.70 ($C_2$, d, $^3J_{C,F}$=17.9 Hz). $^{19}$F NMR ($CD_3SOCD_3$, 376 MHz) ppm −72.81(s). EI-MS 265 (M, 3.8), 248 (M-OH, 5.3), 154 (M-purine base, 100.0). EI-HRMS calcd. for $C_{11}H_{12}N_5O_2F$: 265.0975, found: 265.0974. Calculated for $C_{11}H_{12}N_5O_2F$: C, 49.81; H, 4.56; N, 26.40. Found: C, 49.92; H, 4.70; N, 26.26.

EXAMPLE 26

(E)-2-Amino-6-fluoro-9-{[2,2-bis-hydroxymethyl)cyclo-propylidene]methyl}purine (2p)

The procedure described in Example 25 was perfomed with the E-isomer 2b from Example 10 (0.5 mmol scale) to give compound 2p (107 mg, 81%).

Mp. 214-216° C. UV max 289 nm (ε 8,600), 271 nm (ε 8,800), 229 nm (ε 38,400). $^1$H NMR ($CD_3SOCD_3$, 400 MHz) δ 1.53 (d, 2H, J=1.6 Hz), 3.44, 3.55 and 3.45, 3.49 (2AB, 4H, $J_{AB}$=11.2 Hz), 4.74 (t, 2H, OH, J=5.6 Hz), 7.01 (s, 2H, $NH_2$), 7.33 (s, 1H, $H_{1'}$), 8.42 (s, 1H, $H_8$). $^{13}$C NMR ($CD_3SOCD_3$, 100 MHz) ppm 14.46 ($C_{3'}$), 29.78 ($C_{4'}$), 62.98 ($C_{5'}$), 110.62 ($C_{1'}$), 111.87 ($C_5$, d, $^2J_{C,F}$=31.4 Hz), 120.26 ($C_{2'}$), 139.79 ($C_8$), 156.64 ($C_4$, d, $^3J_{C,F}$=12.0 Hz), 159.88 ($C_6$, d, $^1J_{C,F}$=250.7 Hz), 160.70 ($C_2$, d, $^3J_{C,F}$=17.9 Hz). $^{19}$F NMR ($CD_3SOCD_3$, 376 MHz) ppm −72.6 (s). EI-MS 265 (M, 2.8), 248 (M-OH, 4.0), 154 (M-purine base, 100.0). EI-HRMS calcd. for $C_{11}H_{12}N_5O_2F$: 265.0975, found: 265.0972. Calculated for $CH_{12}N_5O_2F$: C, 49.81; H, 4.56; N, 26.40. Found: C, 49.86; H, 4.68; N, 26.36.

EXAMPLE 27

In Vitro Antiviral Evaluation Methods

Cells and viruses. The routine growth and passage of KB cells was performed in monolayer cultures using minimal essential medium (MEM) with either Hanks salts [MEM(H)] or Earle salts [MEM(E)] supplemented with 10% calf serum. The sodium bicarbonate concentration was varied to meet the buffering capacity required. Cultures of diploid human foreskin fibroblasts (HFF) or MRC-5 cells were grown in medium consisting of MEM(E) with 10% fetal bovine serum. Cells were passaged at 1:2 to 1:10 dilutions according to conventional procedures by using 0.05% trypsin plus 0.02% EDTA in a HEPES buffered salt solution (HBS) (Shipman, C., Jr., *Proc. Soc. Exp. Biol.* 130:305-310 (1969)) as described previously. Turk, S. R., et al., *Antimicrob. Agents Chemother*. 31:544-550 (1987). HFF and MRC-5 cells were passaged only at 1:2 dilutions. CEM cells were maintained in suspension culture as detailed previously. Kucera, L. S., et al., *AIDS Res. Human Retroviruses* 9:307-314 (1993).

Virological procedures. Stock HCMV was prepared by infecting HFF cells at a multiplicity of infection (m.o.i.) of <0.01 plaque-forming units (p.f.u.) per cell. Cell growth medium was changed every four days until cytopathology was evident in all cells (approximately 21 days). Supernatant fluids were retained as the virus stock. High titer HSV-1 stocks were prepared by infecting KB cells at an m.o.i. of <0.1 as detailed previously. Turk, S. R., et al., *Antimicrob. Agents Chemother*. 31:544-550 (1987). Virus titers were determined using monolayer cultures of HFF cells for HCMV and monolayer cultures of BSC-1 cells for HSV-1 as described earlier. Prichard, M. N. et al., *J. Virol. Methods* 28:101-106 (1990). Briefly, HFF or BSC-1 cells were planted as described above in 96-well cluster dishes and incubated overnight at 37° C. in a humidified 3% $CO_2$-97% air atmosphere. The next day cultures were inoculated with HCMV or HSV-1 and serially diluted 1:3 across the remaining eleven columns of the 96-well plate. Cultures were incubated at 37° C. for 2 hr to permit virus adsorption and then virus inoculum was replaced with 0.2 mL of fresh medium. Cultures were incubated for seven days for HCMV, two or three days for HSV-1, medium was removed, and the cell sheets were stained with 0.1% crystal violet in 20% methanol. Plaques were enumerated under 20-fold magnification in wells having the dilution which gave 5 to 20 plaques per well. Virus titers were calculated according to the following formula: Titer (p.f.u./mL)= number of plaques×5×3$^n$; where n represents the nth dilution of the virus used to infect the well in which plaques were enumerated.

Assays for Antiviral Activity. (a) HCMV. The effect of compounds on the replication of HCMV has been measured using a plaque reduction assay. HFF cells in 24-well cluster dishes were infected with approximately 100 p.f.u. of HCMV per cm$^2$ cell sheet using the procedures detailed above. Following virus adsorption, compounds dissolved in growth medium were added to duplicate wells in three to six selected concentrations. Following incubation at 37° C. for 7 to 10 days, cell sheets were fixed, stained with crystal violet and microscopic plaques enumerated as described above. Drug effects were calculated as a percentage of reduction in number of plaques in the presence of each drug concentration compared to the number observed in the absence of drug. Ganciclovir (DHPG) was used as a positive control in all experiments.

The effect of compounds on the replication of HCMV may also be measured using a yield reduction assay. HFF cells were planted as described above in 96-well cluster dishes, incubated overnight, medium removed and the cultures were inoculated with HCMV at a m.o.i. of 0.5 to 1 p.f.u. per cell as reported elsewhere. After virus adsorption, inoculum was replaced with 0.2 mL of fresh medium containing test compounds. The first row of 12 wells was left undisturbed and served as virus controls. Each well in the second row received an additional 0.1 mL of medium with test compound at three times the desired final concentration. The contents of the 12 wells were mixed by repeated pipetting and then serially diluted 1:3 along the remaining wells. In this manner, six compounds could be tested in duplicate on a single plate with concentrations from 100 µM to 0.14 µM. Plates were incubated at 37° C. for seven days, subjected to one cycle of freezing and thawing; aliquots from each of the eight wells of a given column were transferred to the first column of a fresh 96-well monolayer culture of HFF cells. Contents were mixed and serially diluted 1:3 across the remaining eleven columns of the secondary plate. Each column of the original primary plate was diluted across a separate plate in this manner. Cultures were incubated, plaques were enumerated, and titers calculated as described above.

Assays for Antiviral Activity. (b) HSV-1. An enzyme-linked immunosorbent assay (ELISA) was employed to detect HSV-1. 96-well cluster dishes were planted with BSC-1 cells at 10,000 cells per well, in a total volume of 200 µL per well of MEM(E) plus 10% calf serum. After oveinight incubation at 37° C., drug and HSV-1 was added at the rate of 100 PFU/well. ELISA plates were blocked with 200 µL per well of 10% calf serum and 0.05% tween in HBS. After incubation for 30 minutes, the blocking agent was rinsed two times with HBS-T. A 1:400 dilution of AP conjugated rabbit anti-HSV-1 antibody in HBS-F was added. Plates were sealed with adhesive sheet, and incubated on rocker for one hour at 37° C. Plates were developed in the dark with 100 µL per well of substrate solution containing p-nitrophenyl phosphate. Plates were read at 492 nm. Drug effects were calculated as a percentage of the reduction in virus in the presence of each drug concentration compared to the titer obtained in the absence of drug. Acyclovir was used as a positive control in all experiments.

Assays for Antiviral Activity. (c) HHV-6. In this case, enzyme-linked immunosorbent assay (ELISA) was performed in covalent amine plates (Costar, Cambridge, Mass.). The plates were activated by the addition of a homobifunctional crosslinking agent, bis(sulfosuccinimidyl) suberate, which was dissolved at 1 mg/mL in 30 mL of phosphate buffered saline (PBS: 137 mM NaCl, 2.7 mM KCl, 4.3 mM Na$_2$HPO$_4$, 1.4 mM KH$_2$PO$_4$, pH 7.4) and 300 µL of the crosslinker was added to each well in the covalent plate. The crosslinker reacted with the amine function on the plate for 30 min at room temperature. The byproduct, sodium N-hydroxysuccinimide sulfite, was removed by decanting and washing the plate twice with PBS. Samples consisting of 150 µl of mixed suspended HSB$_2$ cells from the original drug-treated plate were solubilized in an equal volume of 10% Triton X-100 in coating buffer (15 mM Na$_2$CO$_3$, 3.5 mM NaHCO$_3$, pH 9.6). The plate was covered and then incubated for 1 h at 37° C. in a 5% CO$_2$ atmosphere. These binding conditions facilitated covalent attachment of the antigen to the free end of the crosslinker.

After covalent binding, the antigen solution was decanted and the plate was washed six times in HEPES buffered saline (Shipman, C., Jr., *Proc. Soc. Exp. Biol.* 130:305-310 (1969)) with 0.05% Tween 20 (HBS-T), soaking for three min for each wash. Unbound sites on the plate were blocked with 300 µL per well of 2% lowfat dry milk in PBS (blocker) for 30 min at room temperature on a shaker. The blocker was decanted and 50 µL of the diluted primary monoclonal antibody, specific for HHV-6 (GS) glycoprotein gp116, was added. The antibody solution consisted of antibody diluted 1:400 in equal volumes of blocker and 10% Triton X-100 in coating buffer. The presence of both blocker and detergent in the antibody solutions was necessary to reduce background signal. The plate was then covered and incubated for 1 h at 37° C. The plate was washed again, as described above, then blocker was added again, as before. Next, each well received 100 µL of a solution of the secondary antibody, horse radish peroxidase-labeled rabbit anti-mouse antibody, diluted to 1:400 (as above). The plate was incubated for 1 h at 37° C. The plate was washed again as described above, and developed using 100 µL/well of TMB-Turbo (Pierce, Rockford, Ill.) for 30 min at room temperature. The reaction was stopped with 50 µL/well 2 M H$_2$SO$_4$. Absorbance in each well was determined at 450/570 nm.

Assaysfor Antiviral Activity. (d) HIV-1. Reverse transcriptase (RT) was employed as a marker for HIV-1. This assay measured the presence of HIV in supernatants of CEM cells infected with strain III$_B$ of HIV-1 by the amount of RT activity. Cells were grown, infected, and incubated in the presence of seven concentrations (one-half log$_{10}$ dilutions) beginning at 1 or 100 µM of compounds to be assayed. Procedures and the RT assay were performed as detailed previously. Kucera, L. S., et al., *AIDS Res. Human Retroviruses* 9:307-314 (1993); White, E. L., et al., *Antiviral Res.* 16:257-266 (1991).

Cytotoxicity assays. Two different assays were used to explore cytotoxicity of selected compounds as we have detailed previously. (i) Cytotoxicity produced in stationary HFF cells was determined by microscopic inspection of cells used in plaque assays which were not affected by the virus. Turk, S. R., et al., *Antimicrob. Agents Chemother.* 31:544-550 (1987). (ii) The effect of compounds during two population doublings of KB cells was determined by crystal violet staining and spectrophotometric quantitation of dye eluted from stained cells. Prichard, M. N., et al., *Antimicrob. Agents Chemother.* 35:1060-1065 (1991).

Data Analysis. Dose-response relationships were constructed by linearly regressing the percent inhibition of parameters derived in the preceding sections against log drug concentrations. Fifty-percent inhibitory ($IC_{50}$) concentrations were calculated from the regression lines. Samples containing positive controls (acyclovir for HSV-1, ganciclovir for HCMV, and 2-acetylpyridine thiosemicarbazone for cytotoxicity) were used in all assays. Results from sets of assays were rejected if inhibition by the positive control deviated from its mean response by >±1.5 standard deviations.

Testing Results. Compounds of Formulas 1 and 2 exhibit a significant activity against herpesviruses. It was found that compounds of the present invention strongly inhibit the replication of HMCV as measured by plaque reduction assays using HFF as host cells by the method described above and they also inhibit the replication of HSV-1 as determined by enzyme-linked immunosorbent assay (ELISA).

TABLE 1

| Compound | $IC_{50}$ (μM) HCMV[a] | $IC_{50}$ (μM) HSV-1[b] |
|---|---|---|
| 1a, Example 8 | 3.6 | 50 |
| 1c, Example 11 | 0.46 | >100 |
| 2c, Example 12 | >100 | 39 |
| 1e, Example 15 | 32 | >100 |
| 1f, Example 18 | >100 | 10 |
| 1g, Example 19 | 3.5 | >100 |
| 1o, Example 23 | 15 | >100 |
| Control | 4.1[c] | 0.15[d] |

[a]Plaque reduction.
[b]ELISA.
[c]Ganciclovir.
[d]Acyclovir.

The effects against HCMV are better than those of ganciclovir, current drug of choice for HCMV.

Compounds of the present invention were tested for cytotoxicity in a culture of HFF and KB cells according to the methods described above. These tests indicate a complete lack of cytotoxicity for tested compounds that have antiviral activity.

TABLE 2

| Compound | IC50 (μM) HFF (visual) | IC50 (μM) KB (growth) |
|---|---|---|
| 1a, Example 8 | >100 | >100 |
| 1c, Example 11 | >100 | >100 |
| 2c, Example 12 | >100 | >100 |
| 1e, Example 15 | >100 | >100 |
| 1f, Example 18 | >100 | >100 |
| 1g, Example 19 | >100 | >100 |
| 1o, Example 23 | >100 | >100 |
| Control | >100[a] | >100[b] |

[a]Ganciclovir.
[b]Acyclovir.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings and specification.

All patents and other publications cited herein are expressly incorporated by reference.

What is claimed is:

1. A compound having the formula:

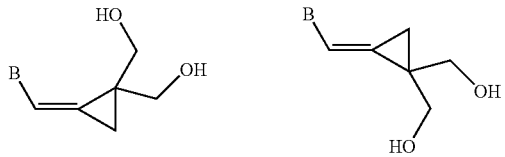

wherein B is a purine heterocyclic ring, and pharmaceutically acceptable salts and prodrugs thereof.

2. The compound of claim 1, wherein the purine is selected from the group consisting of adenine, hypoxanthine, guanine, 2-amino-6-substituted purine, 2-amino-6-chloropurine, 2-amino-6-fluoropurine, 2-amino-6-alkoxypurine, 2,6-diaminopurine, 2-amino-6-alkylaminopurine, 2-amino-6-dialkylaminopurine, 2-amino-6-thiopurine, and 2-amino-6-alkylthiopurine.

3. An antiviral compound selected from the group consisting of (Z)-9-{[2,2-bis-(hydroxy-methyl)cyclopropylidene]methyl}adenine (1a), (Z)-2-amino-6-chloro-9-{[2,2-bis-(hydroxymethyl)cyclo-propylidene]methyl}purine (1 b), (Z)-9-{[2,2-bis-(hydroxymethyl)cyclo-propylidene]methyl}guanine (1c), (Z)-2-amino-6-methoxy-9-{[2 ,2-bis-(hydroxymethyl)cyclopropylidene]methyl}purine (1g), (Z)-2-amino-6-cyclopropylamino-9-{[2,2-bis-(hydroxymethyl)-cyclopropylidene]-methyl}purine (1h), (Z)-2-amino-6-allylamino-9-{[2,2-bis-(hydroxymethyl)cyclo-propylidene]methyl}purine (1i), (Z)-2-amino-6-propargylamino-9-{[2,2-bis-(hydroxymethyl)cyclo-propylidene]methyl}-purine (1j), (Z)-2-amino-6-cyclopropylmethylamino-9-{[2,2-bis-(hydroxymethyl)cyclopropylidene]methyl}purine (1k), (Z)-2-amino-6-propyloxy 9-{[2,2-bis-(hydroxymethyl) cyclopropylidene]-methyl}purine (1l), (Z)-2-amino-6-allyloxy-9-{[2,2-bis-(hydroxy-methyl)cyclopropylidene] methyl}purine (1m), (Z)-2-amino-6-propylthio-9-{[2,2-bis-(hydroxymethyl)cyclopropylidene]-methyl}purine (1n), (Z)-2,6-diamino-9-{[2,2-bis-(hydroxymethyl) cyclopropylidene]-methyl}purine (1o), and (Z)-2-amino-6-fluoro-9-{[2,2-bis-(hydroxy-methyl)cyclo-propylidene] methyl}purine (1p).

4. An antiviral compound selected from the group consisting of (E)-9-{[2,2-bis-(hydroxymethyl)cyclopropylidene]methyl}adenine (2a), (E)-2-amino-6-chloro-9-{[2,2-bis-(hydroxymethyl)cyclopropylidene]-methyl}purine (2b), (E)-9-{[2,2-bis-(hydroxymethyl)cyclo-propylidene]methyl}guanine (2c), (E)-2-amino-6-methoxy-9-{[2,2-bis-(hydroxymethyl)cyclopropylidene]methyl}purine (1g), (E)-2-amino-6-cyclopropylamino-9-{[2,2-bis-(hydroxy-methyl) cyclopropylidene]methyl}purine (2h), (E)-2-amino-6-allylamino-9-{[2,2-bis-(hydroxymethyl)cyclopropylidene] methyl}purine (2i), (E)-2-amino-6-propargylamino-9-{[2,2-bis-(hydroxymethyl)cyclo-propylidene]methyl}purine (2j), (E)-2-amino-6-cyclopropylmethylamino-9-{[2,2-bis (hydroxymethyl)cyclopropylidene]methyl}purine (2k), (E)-2-amino-6-propyloxy-9-{[2,2-bis-(hydroxymethyl)cyclopropylidene]-methyl}purine (2l), (E)-2-amino-6-allyloxy-9-{[2,2-bis-(hydroxymethyl)-cyclopropylidene] methyl}purine (2m), and (E)-2-amino-6-propylthio-9-{[2,2-bis-(hydroxymethyl)cyclo-propylidene]methyl}purine (2n) (E)-2,6-diamino-9-{[2,2-bis-(hydroxymethyl)cyclopropylidene]-methyl}purine (2o), and (E)-2-amino-6-fluoro-9-{[2,2-bis-(hydroxy-methyl)cyclo-propylidene]methyl}purine (2p).

5. A composition comprising a compound of any one of claims 1, 2, 3, or 4 and a pharmaceutically acceptable carrier.

6. A method of treating of a mammal infected with a virus selected from the group consisting of HHV, VZV, HCMV, EBV, HSV-1, and HSV-2 comprising a step of administering to said mammal a compound according to any one of claims 1, 2, 3, or 4 and combinations thereof.

7. The method of claim 6, wherein said mammal is a human.

8. The method of claim 6, further comprising a step of administering an additional compound.

9. The method of claim 8, wherein said additional compound is selected from the group consisting of acyclovir, ganciclovir, zidovudine, AZT, ddl, ddc, 3TC, d4T, foscarnet, cidofovir, fomivirsen, and combinations thereof.

* * * * *

UNITED STATES PATENT AND TRADEMARK OFFICE
CERTIFICATE OF CORRECTION

PATENT NO. : 7,393,855 B2
APPLICATION NO. : 10/942313
DATED : July 1, 2008
INVENTOR(S) : Jiri Zemlicka et al.

It is certified that error appears in the above-identified patent and that said Letters Patent is hereby corrected as shown below:

On the Title page, item 54, in the title, replace "PYRIMIDINES" with -- -PYRIMIDINES --.

In column 1, line 3, in the title, replace "PYRIMIDINES" with -- -PYRIMIDINES --.

Signed and Sealed this

Sixteenth Day of September, 2008

JON W. DUDAS
*Director of the United States Patent and Trademark Office*